US 6,609,521 B1

(12) United States Patent
Belani et al.

(10) Patent No.: US 6,609,521 B1
(45) Date of Patent: Aug. 26, 2003

(54) ENDOTRACHEAL TUBE

(75) Inventors: Kumar G. Belani, Edina, MN (US); Michael F. Sweeney, St. Paul, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 57 days.

(21) Appl. No.: 09/832,325

(22) Filed: Apr. 9, 2001

(51) Int. Cl.[7] ........................ A61M 16/00; A61M 29/00
(52) U.S. Cl. ........................ 128/207.14; 128/207.15; 604/96.01
(58) Field of Search ................ 128/207.14–207.16, 128/207.18, 206.29, 206.21, 204.18, 200.24, 200.26; 604/96.01, 246, 247, 523; 600/432–435

(56) References Cited

U.S. PATENT DOCUMENTS

| | | | | |
|---|---|---|---|---|
| 4,166,468 A | * | 9/1979 | Haynie | 128/207.15 |
| 4,233,984 A | * | 11/1980 | Walling | 128/207.14 |
| 4,248,236 A | * | 2/1981 | Linder | 206/364 |
| 4,327,720 A | * | 5/1982 | Bronson et al. | 128/207.15 |
| 4,453,545 A | * | 6/1984 | Inoue | 128/207.15 |
| 4,819,664 A | * | 4/1989 | Nazari | 128/207.15 |
| 4,840,172 A | * | 6/1989 | Augustine et al. | 128/207.14 |
| 4,924,862 A | | 5/1990 | Levinson | 128/207.16 |
| 5,033,466 A | * | 7/1991 | Weymuller, Jr. | 128/200.26 |
| 5,067,497 A | * | 11/1991 | Greear et al. | 128/207.15 |
| 5,083,561 A | | 1/1992 | Russo | 128/207.16 |
| 5,203,771 A | | 4/1993 | Melker et al. | 604/53 |
| 5,218,970 A | | 6/1993 | Turnbull | 128/748 |
| 5,235,973 A | | 8/1993 | Levinson | 128/207.15 |
| 5,309,906 A | * | 5/1994 | LaBombard | 128/207.14 |
| 5,315,992 A | | 5/1994 | Dalton | 128/207.15 |
| 5,318,021 A | | 6/1994 | Alessi | 128/207.15 |
| 5,360,403 A | * | 11/1994 | Mische | 604/101.02 |
| 5,443,060 A | | 8/1995 | Visveshwara et al. | 128/200.26 |
| 5,487,383 A | | 1/1996 | Levinson | 128/207.15 |
| 5,499,625 A | | 3/1996 | Frass et al. | 128/207.15 |
| 5,507,279 A | * | 4/1996 | Fortune et al. | 128/200.26 |
| 5,588,424 A | | 12/1996 | Insler et al. | 128/207.15 |

(List continued on next page.)

FOREIGN PATENT DOCUMENTS

| | | | |
|---|---|---|---|
| DE | 19826690 | 11/1999 | A61M/16/20 |
| EP | 0010880 | 5/1980 | A61M/16/00 |
| GB | 2122095 | 1/1984 | A61M/16/00 |
| WO | 99/07428 | 2/1999 | A61M/16/04 |
| WO | 00/32262 | 6/2000 | A61M/16/04 |

OTHER PUBLICATIONS

Duke, P.M., et al., "Cleft palate associatd with prolonged orotracheal intubation in infancy", *The Journal of Pediatrics*, 89 (6), pp. 990–991, (Dec. 1976).

Erenberg, A., et al., "Appliance for stabilizing orogastric and orotracheal tubes in infants", *Critical Care Medicine*, 12 (8), pp. 669–671, (Aug. 1984).

(List continued on next page.)

*Primary Examiner*—Weilun Lo
*Assistant Examiner*—Teena Mitchell
(74) *Attorney, Agent, or Firm*—Schwegman, Lundberg, Woessner & Kluth, P.A.

(57) ABSTRACT

An endotracheal tube has a proximal end and a distal end and includes a tracheal portion having an opening at the proximal end and a bronchial portion attached at an angle to the tracheal portion. The bronchial portion has an opening at the distal end of the endotracheal tube. A balloon is positioned within the endotracheal tube that blocks the flow of a gas through the bronchial portion of the endotracheal tube when inflated. The endotracheal tube has an opening between the proximal end and the balloon. The opening is positioned to allow ventilation of the lung opposite the lung into which the bronchial portion is adapted to extend into. The endotracheal tube may include a carinal seating mechanism which may be located near the junction between the tracheal portion and the bronchial portion of the endotracheal tube. The endotracheal tube further may also include an inflatable bronchial extension tube.

33 Claims, 16 Drawing Sheets

U.S. PATENT DOCUMENTS

| | | | | |
|---|---|---|---|---|
| 5,607,386 A | * | 3/1997 | Flam | 128/200.26 |
| RE35,595 E | * | 8/1997 | Six | 128/200.26 |
| 5,660,175 A | | 8/1997 | Dayal | 128/207.15 |
| 5,697,365 A | | 12/1997 | Pell | 128/207.15 |
| 5,718,225 A | | 2/1998 | Visveshwara et al. | 128/200.26 |
| 5,728,068 A | | 3/1998 | Leone et al. | 604/101 |
| 5,765,559 A | | 6/1998 | Kim | 128/207.15 |
| 5,791,338 A | * | 8/1998 | Merchant et al. | 128/200.26 |
| 5,846,087 A | | 12/1998 | Scherer | 434/270 |
| 5,865,176 A | * | 2/1999 | O'Neil | 128/207.15 |
| 5,884,625 A | | 3/1999 | Hart | 128/207.14 |
| 5,904,648 A | | 5/1999 | Arndt et al. | 600/120 |
| 5,906,204 A | | 5/1999 | Beran et al. | 128/207.14 |
| 5,915,383 A | | 6/1999 | Pagan | 128/207.15 |
| 5,919,183 A | * | 7/1999 | Field | 128/200.26 |
| 5,947,120 A | | 9/1999 | Bailey | 128/207.14 |
| 5,950,624 A | | 9/1999 | Hart | 128/207.15 |
| 5,976,072 A | | 11/1999 | Greenberg | 600/120 |
| 6,153,527 A | * | 11/2000 | Jost et al. | 438/696 |
| 6,257,236 B1 | * | 7/2001 | Dutkiewicz | 128/200.26 |
| 6,287,290 B1 | * | 9/2001 | Perkins et al. | 604/509 |
| 6,378,521 B1 | * | 4/2002 | Van Den Berg | 128/200.26 |
| 6,390,988 B1 | * | 5/2002 | Robinson | 128/204.18 |
| 6,398,775 B1 | * | 6/2002 | Perkins et al. | 604/164.03 |
| 6,427,692 B1 | * | 8/2002 | Hoglund | 128/205.24 |
| 6,443,156 B1 | * | 9/2002 | Niklason et al. | 128/207.14 |
| 2002/0185135 A1 | * | 12/2002 | Amar | 128/207.15 |
| 2003/0015192 A1 | * | 1/2003 | Teves | 128/200.26 |

OTHER PUBLICATIONS

Erenberg, A., et al., "Palatal Groove Formation in Neonates and Infants With Orotracheal Tubes", *American Journal of Diseases of Children, 138* (*10*), pp. 974–975, (Oct. 1984).

Fadavi, S., et al., "An Intraoral Prosthetic Appliance for the Prevention of Palatal Grooving in Premature Intubated Infants", *Clinical Preventive Dentistry, 12* (*1*), pp. 9–12, (1990).

Fadavi, S., et al., "The oral effects of orotracheal intubation in prematurely born preschoolers", *Journal of Dentistry for Children*, pp. 420–424, (Nov./Dec. 1992).

Fadavi, S., et al., "Use of a palatal stabilizing device in prevention of palatal grooves in premature infants", *Critical Care Medicine, 18* (*11*), pp. 1279–1281, (1990).

Ginoza, G.W., et al., "Prevention of Palatal Groove Formation with Prolinged Orotracheal Intubation in Preterm Infants", *Pediatric Research, 25* (*4*), Part 2, Abstract No. 1276, p. 215A, (Apr. 1989).

Hammer, G.B., et al., "Methods for SIngle–Lung Ventilation in Pediatric Patients", *Anesth. Analg., 89*, pp. 1426–1429, (1999).

Molteni, R.A., et al., "Development and Severity of Palatal Grooves in Orally Intubated Newborns", *American Journal of Diseases of Children, 140* (*3*), pp. 357–359, (Apr. 1986).

Rotschild, A., et al., "Midfacial Hypoplasia Associated With Long–term Intubation for Bronchopulmonary Dysplasia", *American Journal of Diseases of Children, 144* (*12*), pp. 1302–1306, (Dec. 1990).

Saunders, B.S., et al., "Acquired palatal groove in neonates", *The Journal of Pediatrics, 89* (*6*), pp. 988–989, (Dec. 1976).

Sullivan, P.G., "An Appliance to Support Oral Intubation in the Premature Infant", *British Dental Journal, 152* (*6*), pp. 191–195, (Mar. 1982).

\* cited by examiner

ENDOTRACHEAL TUBE

FIELD OF THE INVENTION

The present invention relates to the field of endotracheal tubes. More particularly, this invention deals with an apparatus and process for placing an endotracheal tube so that one or both lungs may be ventilated during an operation.

BACKGROUND OF THE INVENTION

It is a common practice to provide human medical patients with artificial ventilation during surgery or in emergency situations. For example, accident victims will frequently require CPR or intubation by a paramedic in an emergency vehicle or by an anesthesiologist in an operating room. There are other surgical procedures which require use of an endotracheal tube to collapse one lung. For example, taking a biopsy from the lung to gather information on an infection, repairing a lobar defect due to infant emphysema, removing tumors, repairing an abscess or doing an esophageal triage. Generally, an endotracheal tube for collapsing one lung requires two separate passages, or "lumens".

Intubation is accomplished by insertion of an endotracheal tube through the patient's mouth or nasal passages into the airway passage. Such devices have generally comprised a relatively pliable tube with means for connecting it to a respirator or other air supply mechanism for introduction of air into the lungs. An improvement to endotracheal tubes includes an inflatable/deflatable bag-like structure or balloon "cuff" around the exterior of the tube. The balloon cuff is conventionally located in a position along the endotracheal tube to engage the inner wall of the pharynx, larynx, or trachea depending upon the specific endotracheal tube design. When the tube is in place, the cuff is inflated and forms an air tight seal between the tube and the surrounding body tissue to prevent the escape of air pumped from the respirator into the lungs.

Both single lumen and double lumen endotracheal tubes are known. Typically, a single lumen endotracheal tube is an elongated tube that extends into the trachea of a patient upon intubation and includes one inflatable balloon cuff near its distal end. Commonly, the double lumen endotracheal tube is referred to as an endobronchial tube and, in addition to one lumen which extends to the trachea, has a second longer lumen which extends into the bronchus of a patient upon intubation. Typically, the double lumen endotracheal tube or endobronchial tube includes two inflatable balloon cuffs. The so-called double lumen endobronchial tubes, such as the well known "Carlens" and "Robertshaw" tubes, allow for independent control of each lung through the separate lumina. One bronchus may be blocked by occluding one of the lumina at a position external to the patient, in order to isolate a particular lung.

The balloon cuffs are thin walled, high volume, and low pressure chambers or vessels which are designed not to compromise the blood flow in the tracheal or bronchial wall when inflated. Balloon cuffs are inflated by detachable syringes that are connected to smaller lumina or channels at the proximal end of the endotracheal tube. The seals formed by the inflated cuffs preclude the air that has been forced into the patient's lungs from escaping through the trachea or bronchus. Additionally, the seals formed by the inflated cuffs provide a barrier to the flow of blood, mucus, and secretions.

The so-called double lumen endobronchial tubes also offer anesthesiologists the ability to insufflate selectively either the right or left lung or both lungs as required. The so-called double lumen endobronchial tubes also offer the physician the ability to collapse either lung as needed for certain procedures. The size of endotracheal tubes and endobronchial tubes is limited. In order to minimize damage to the tissue on the tracheal wall, the overall outer diameter of both single and double lumen endobronchial tubes is limited to approximately 1.2 cm. For this reason, the inner diameter of each lumen of a double lumen endobronchial tube is by necessity smaller than the inner diameter of a single lumen endotracheal tube. As a result, the inner diameter of the single lumen endotracheal tube can typically be no more than about 7.5 mm; whereas, the inner diameter of each lumen in a double lumen endobronchial tube is limited to a maximum of approximately 3.5 mm.

When an endotracheal tube is needed for pediatric use, the size limitations are even more restrictive. In pediatric patients, the size of the trachea is approximately the same size as the patient's pinky finger. The size limitations virtually eliminate double lumen endotracheal tubes for infants since one or both of the lumens must have such a small diameter that the volumes of air or other gas that can be moved through the small lumen are less than that required by the patient. As a result, a single lumen endotracheal tube is required for procedures involving infant or toddler pediatric patients.

In pediatric patients, a single lumen endotracheal tube is advanced into the bronchus until breath sounds on the operative lung disappear. A fiberoptic bronchoscope may be passed along the endotracheal tube to confirm or guide placement of the endotracheal tube. There may be problems with such a procedure. The problems include incomplete collapse of the operated lung or failure to prevent contamination of the healthy, ventilated lung. Other techniques include use of two single lumen endotracheal tubes (one to each lung), use of a bronchial blocker to seal the lung and cause it to collapse. Use of a bronchial blocker generally requires more time than the previous method.

The larger lumen provided in a single lumen endotracheal tube affords the anesthesiologist access for other instrumentation through the lumen as required. The removal of mucus, the injection of medication, or the insertion of fiberoptic instrumentation for viewing within the endotracheal tube are examples of the additional instrumentation capability which is afforded by a single lumen tube. The ability to insert fiberoptic instrumentation through the tube significantly aids the anesthesiologist during intubation to accurately determine if the endobronchial tube is correctly positioned within the trachea and bronchus of the patient. These capabilities are restricted, if not prohibited, in the double lumen endobronchial tubes which by necessity have more narrow inner diameter passages and afford less access through the tubes by the anesthesiologist for the probes and instrumentation described.

For these and other reasons both prior art single and double lumen tubes are not fully satisfactory. There is a need for an endotracheal tube that can be inserted and quickly located in the correct position. There is also a need for an endotracheal tube that can be used to collapse one lung while ventilating the other lung. There is also a need for a single lumen endotracheal tube that can be used in pediatric patients. There is also a need for catheters that can be sealed at their distal ends.

SUMMARY OF THE INVENTION

The present invention is directed to an endotracheal tube which can be inserted through the mouth or nose and past the larynx of a patient and into the tracheal and mainstem bronchial passages. Extending from the tracheal portion of the tube is a bronchial portion which may be placed in either the left or right mainstem bronchus (singular) of the patient. The bronchial portion is angled with respect to the tracheal portion. The size of the angle corresponds to the angle between the trachea and the mainstream bronchus of the patient. Generally, these angles are age dependent and are known. The single lumen of the endobronchial tube of the present invention has an inner diameter sufficient to allow access through the single lumen to the patient's lungs and respiratory system with additional instrumentation, as required. The bronchial portion of the endotracheal tube has a balloon situated on the inside of the tube which can be inflated or deflated. By inflating the balloon, the lung into which the bronchial portion has been advanced can be collapsed so that selected surgical procedures may be performed on the collapsed lung.

Positioned along the tracheal portion of the endobronchial tube of the present invention is at least one external balloon cuff which can be selectively inflated and deflated. When inflated, the tracheal balloon cuffs prevent retrograde air from escaping between the endotracheal tube and the trachea. Positioned between the external tracheal balloon cuff and the distal end of the endotracheal tube is an air outlet port from the tube through which oxygen from a respirator input to the endobronchial tube can escape into the patient's respiratory system in order to ventilate at least one of the lungs. In one embodiment of the invention, the opening includes an extendable tube which can be inflated to extend it into the bronchus of the patient.

Located at a distal end of the bronchial portion of the endobronchial tube is a second air outlet port through which air may exit to allow successful collapse of the lung. Thus this acts as a vent. The internal bronchial balloon serves to provide a seal so that the collapsed lung is not ventilated when the tracheal portion is actively ventilated. The second air outlet may also be used to provide oxygen at low flows when deemed necessary clinically.

An endotracheal tube has a proximal end and a distal end and includes a tracheal portion having an opening at the proximal end and a bronchial portion attached at an angle to the tracheal portion. The bronchial portion has an opening at the distal end of the endotracheal tube. A balloon is positioned within the endotracheal tube. The balloon blocks the flow of gas through the bronchial portion of the endotracheal tube when inflated. The endotracheal tube also has an opening positioned between the proximal end and the balloon. The opening in the endotracheal tube between the proximal end and the balloon is positioned to allow ventilation of the lung opposite the lung into which the bronchial portion is adapted to extend into. The endotracheal tube further includes an inflatable bronchial extension tube having a first end and second end. One of the first end and the second end corresponds to the opening in the endotracheal tube positioned between the proximal end and the balloon and the other of the first end and the second end adapted to extend into a bronchus of a patient when inflated. In some embodiments, the endotracheal tube also includes a cuff positioned around the end of the bronchial extension tube adapted to extend into a bronchus of a patient when inflated. The cuff is separately inflatable from the inflatable bronchial extension tube. In other embodiments, the balloon positioned within the end of the bronchial extension tube is adapted to extend into a bronchus of a patient when inflated. The balloon is separately inflatable from the inflatable bronchial extension tube. The inflatable bronchial extension tube may include a bellows. The inflatable bronchial extension tube may also be adapted to extend at a selected angle from the tracheal portion of the endotracheal tube.

In some embodiments, the endotracheal tube may include a carinal seating mechanism which may be located near the junction between the tracheal portion and the bronchial portion of the endotracheal tube. The carinal seating mechanism is made of foam rubber. The carinal seating mechanism extends beyond the outer periphery of the endotracheal tube at a distance such that it does not interfere with passing the endotracheal tube through the trachea of a patient yet is at a distance adapted to seat against the carina of a patient. In some embodiments, the endotracheal tube includes an external inflatable cuff positioned on the tracheal portion of the endotracheal tube. In other embodiments, the endotracheal tube includes a first external inflatable cuff positioned on the tracheal portion of the endotracheal tube, and a second external inflatable cuff positioned on the bronchial portion of the endotracheal tube. The endotracheal tube further includes one or more channels having a distal end and a proximal end. The distal end of the channel is attached to an inflatable portion of the endotracheal tube and the proximal end of the one or more channels is positioned near the proximal end of the endotracheal tube. The angle between the bronchial portion and the tracheal portion of the endotracheal tube varies based on the age of the patient.

A method of inserting an endotracheal tube having a tracheal portion, a bronchial portion attached at an angle to the tracheal portion, and a carinal seating mechanism includes inserting the endotracheal tube through the trachea until the carinal seating mechanism is positioned at or near the site of the carina of a patient. The method may include guiding the endotracheal tube to a position where the carinal seating mechanism is positioned near the site of the carina of a patient using a fiberoptic device, or verifying that the carinal seating mechanism of the endotracheal tube is positioned near the site of the carina of a patient using a fiberoptic device.

Another embodiment of the endotracheal tube includes a tracheal portion having an opening at the proximal end of the endotracheal tube, a first bronchial portion attached at an angle to the tracheal portion and having a first open distal end, a second bronchial portion attached at an angle to the tracheal portion and having a second open distal end, and at least one balloon positioned within the endotracheal tube. The balloon blocks the flow of a gas through one of the first and second bronchial portions of the endotracheal tube when inflated. In some embodiments, the endotracheal tube may include an external inflatable cuff positioned on the tracheal portion of the endotracheal tube. In other embodiments, the endotracheal tube includes a first external inflatable cuff positioned on the tracheal portion of the endotracheal tube, and a second external inflatable cuff positioned on one of the first or second bronchial portions of the endotracheal tube. In still other embodiments, a third external inflatable cuff is positioned on the second bronchial portion of the endotracheal tube. The angle between the first bronchial portion and the tracheal portion of the endotracheal tube varies based on the age of the patient. The angle between the second bronchial portion and the tracheal portion of the endotracheal tube varies based on the age of the patient. At least one balloon is positioned within one of the first or the second bronchial portions of the endotracheal tube. In other embodiments, a second balloon is positioned within the other of the first or the second bronchial portions of the endotracheal tube. Each balloon is independently inflatable. The endotracheal tube may include a stylus. The endotracheal tube is adapted to receive the stylus through the tracheal portion and at least one of the first or second bronchial portions. In yet another embodiment, the endotracheal tube further includes at least one external cuff positioned on the tracheal portion of the endotracheal tube.

A method of inserting an endotracheal tube having a tracheal portion, a first bronchial portion attached at an angle to the tracheal portion, and a second bronchial portion attached at an angle to the tracheal portion, includes inserting a stylus into the endotracheal tube. The stylus passes through the tracheal portion and into one of the first or the second bronchial portions of the endotracheal tube. The endotracheal tube and stylus are inserted through the trachea and into a desired bronchus of the patient. The stylus is then removed. In one embodiment, the method further includes using a fiberoptic device to guide the endotracheal tube to a position where one of the first bronchial portion or the second bronchial portion is positioned in the selected bronchus of the patient. In another embodiment, the fiberoptic device is used to verify that the endotracheal tube is positioned such that one of the first bronchial portion or the second bronchial portion is positioned in the selected bronchus of the patient. The fiberoptic device may also be used to verify that both the first bronchial portion and the second bronchial portion are positioned in the selected bronchi of the patient.

Advantageously, the preferred embodiments of the endotracheal tubes described can be inserted and quickly located in the correct position while minimizing trauma to the various portions of the patient. The time required to perform this procedure is also minimized which saves a surgeon time in the operating room and also minimizes the amount of time the patient is under anesthesia. The endotracheal tubes can be used to collapse one lung while ventilating the other lung. The endotracheal tubes also have a single lumen and can be used in all types of patients, especially pediatric patients where double lumen endotracheal tubes cannot provide the necessary air flow through two smaller lumens. There is also a need for catheters that can be sealed at their distal ends. The endotracheal tubes described allow ventilation of either one or both lungs in infants and small children. A left or right endotracheal tube may be used allowing occlusion of one lung. The non-ventilated lung will allow for better surgical access either to the lung itself or to structures surrounding the lung. In addition, the device should accommodate the larger trachea and bronchial airway of older children, young adults, as well as all adults. The design is simple and incorporates a single lumen tube capable of isolating each lung by an internal cuff or balloon. The single lumen favors ease of placement.

The endotracheal tube described also enhances procedures requiring anesthesia during thoracic surgery in infants and children: for example, surgery on the lung for tumors, abscesses, or other lung abnormalities; or around the lung, e.g., esophageal stricture or tumor. The device is particularly effective in preventing trans-bronchial spread of blood and infectious secretions during surgery, while providing improved surgical access to the affected lung when one lung ventilation is deemed necessary. The endotracheal tube may also be useful in the pediatric intensive care unit, when severely asymmetric pulmonary disease exists.

The use of the described endotracheal tube will eliminate the surgeon's and anesthesiologist's need to use a variety of more cumbersome techniques, with tubes and bronchoscopes and will increase the availability of one-lung ventilation during anesthesia and surgery or ICU management of pediatric patients.

BRIEF DESCRIPTION OF THE DRAWINGS

The invention itself, as well as a preferred mode of use, further objects, and advantages thereof, will best be understood by reference to the following detailed description of an illustrative embodiment when read in conjunction with the accompanying drawings, wherein.

DESCRIPTION OF THE PREFERRED EMBODIMENT

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

Figure 1A:
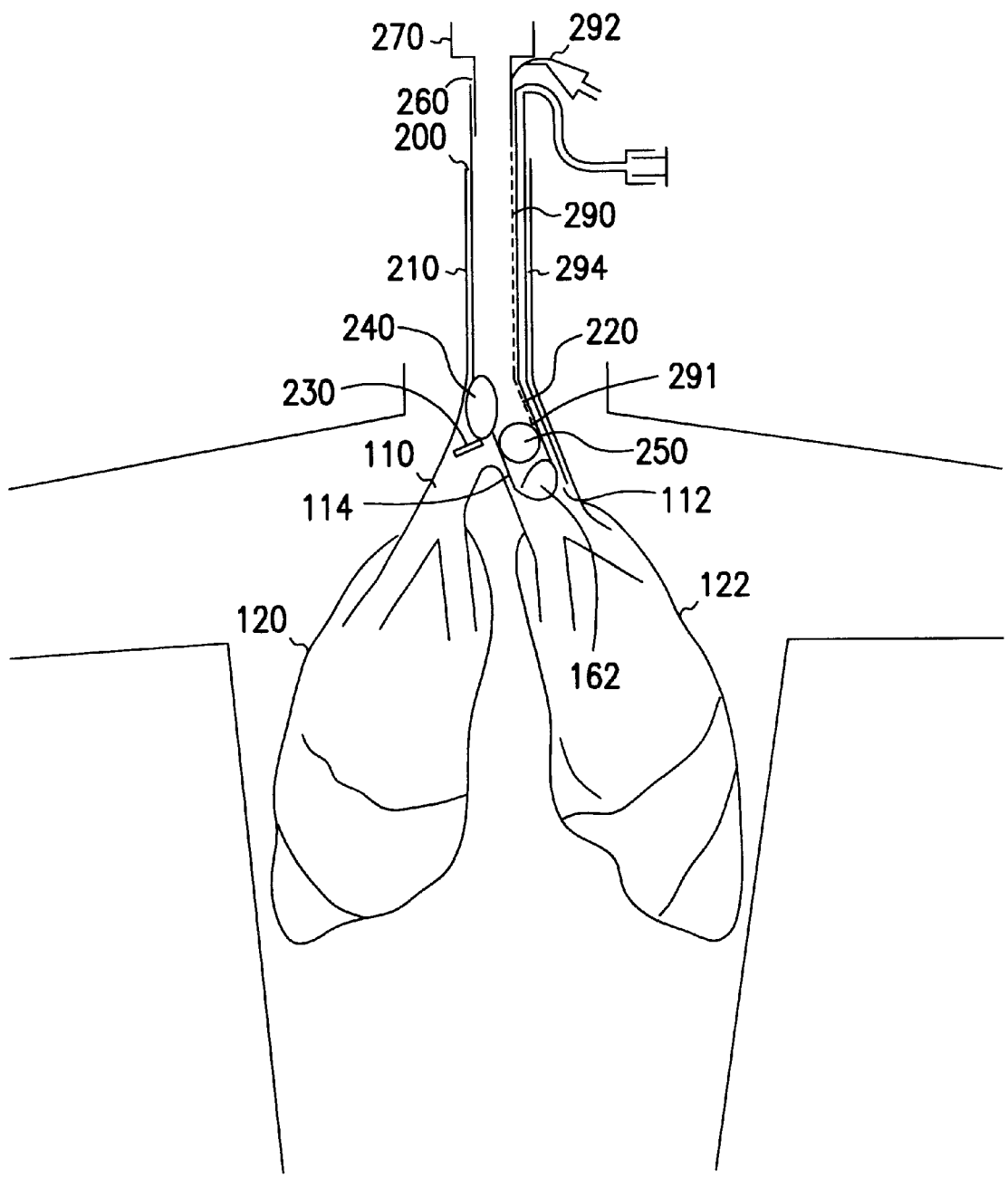
FIG. 1A is a schematic diagram of one preferred embodiment of the endotracheal tube invention for a left endotracheal tube as inserted within the trachea and bronchus of a patient.

FIG. 1A is a schematic diagram of one preferred embodiment of the endotracheal tube 200 for a left endotracheal tube as inserted within the trachea and left primary bronchus 112 of a patient. A patient includes a first lung 120 and a second lung 122. The trachea divides into a right primary bronchus 110 and a left primary bronchus 112. The bronchi 110, 112 then further divide as it enters the lung 120, 122, respectively. The patient includes an oral cavity, a pharynx and a larynx. The right primary bronchus 110 and the left primary bronchus 112 form a Y-shaped structure. The carina 114 is the branched portion at the crotch of the Y between the right primary bronchus 110 and the left primary bronchus 112.

The endotracheal tube 200 includes a tracheal portion 210 and a bronchial portion 220. The bronchial portion 220 is attached and makes an angle with respect to the tracheal portion 210. The size of the angle depends upon the angle between the right primary bronchus 110 and the left primary bronchus 112. As is well known, this angle varies with the age of the patient. Generally, the younger the patient, the less pronounced the angle.

Located on the exterior surface of the endotracheal tube is a carinal seating mechanism 230. When properly positioned, the carina seating mechanism 230 of the endotracheal tube 200 abuts or is positioned near the carina 114. The carina seating mechanism is a small seating cushion that occurs at the angulation and helps position the endotracheal tube 200 so that the endotracheal tube 200 can be placed initially by feel or blindly. The carinal seating mechanism is made of a soft foam and extends from the exterior surface of the endotracheal tube at a distance which is less than a distance that will interfere with the passing of the endotracheal tube 200 through the oral cavity, the pharynx, and the larynx, through the trachea and into the right or left primary bronchus 110, 112. It should be noted that in the particular FIG. 1B, the bronchial portion 220 of the endotracheal tube 200 extends into the left primary bronchus.

The endotracheal tube 200 also includes an opening which is positioned near the carina 114 and facing the opposite lung or opposite primary bronchus. As shown in FIG. 1A, the opening 240 is positioned on the endotracheal tube above the angulation between the tracheal portion 210 and the bronchial portion 220. The opening 240 is also placed above the carinal seating mechanism 230. The endotracheal tube 200 also includes an intraluminal cuff 250 which can be inflated or deflated with air or another gas or other substance. The intraluminal cuff 250 is also referred to as an intraluminal balloon and when inflated occludes or blocks the bronchial portion 220 of the endotracheal tube 200. When inflated, the intraluminal cuff or balloon 250 seals off ventilation to the left lung 122 and allows it to collapse so that a surgical procedure may be accomplished. Meanwhile the right lung 120 is ventilated through the opening 240 near the carina. It should be noted that the bronchial portion 220 has an outer diameter which is selected so that it forms a seal between the right primary bronchus 112 and the bronchial portion 220. The endobronchial tube has a proximal end 260 and a distal end 262. The proximal end 260 is adapted to receive an endotracheal tube adaptor 270.

The endotracheal tube 200 also includes a small lumen or channel which is much smaller than the single lumen of the endotracheal tube 200. The small lumen or channel 290 includes a first end which is attached to the balloon 250 and a second end 292 which is proximate to the proximal end 260 of the endotracheal tube 200. The proximal end 260 includes an inflation and deflation port 292 adapted to receive a syringe. The syringe is then used to inflate the balloon or intraluminal cuff 250 in the bronchial portion 220 of the endotracheal tube 200. The endotracheal tube 200 can also have additional lumens or small channels which function as a vent for the occluded lung or also function as a route to provide jet ventilation of one lung or oxygen insufflation to one lung. The additional lumen or channel 294 has a luerlock connection which can be kept closed or open. The lumen 294 can also incorporate a pop-off valve to release 30 to 60 cm water pressure. It should be noted that the endotracheal tube 200 is essentially a single lumen tube with one large lumen forming the tracheal portion 210 and the bronchial portion 220. The channels 290 and 294 are small when compared to the large single lumen of the endotracheal tube 200.

In operation, the endotracheal tube 200 is placed into the oral cavity of the patient and placed past the pharynx and the larynx through the trachea and into the left bronchus 112 until the carinal seating mechanism 230 catches the carina 114 of the patient. The particular outer diameter of the bronchial portion 220 is selected based upon the age of the patient. It also should be noted that the age of the patient determines both the angle between the bronchial portion 220 and the tracheal portion 210 of the endotracheal tube as well as the outer diameter of the tracheal portion and the outer diameter of the bronchial portion 220. Once the endotracheal tube 200 is positioned within the trachea and bronchus 112 of the patient, a fiberoptic device such as a fiberoptic bronchoscope is used to verify that the placement of the endotracheal tube 200 is correct. The port 292 for the channel 290 is then used to inflate the balloon or intraluminal cuff 250 so that an appropriate surgical procedure may be performed on the collapsed lung 122. Meanwhile the lung 120 is ventilated via the opening 240 in the endotracheal tube 200. The additional channel or lumen 294 can be used to provide ventilation or oxygen support of one lung or it can function as a vent for the occluded lung.

Figure 1B:
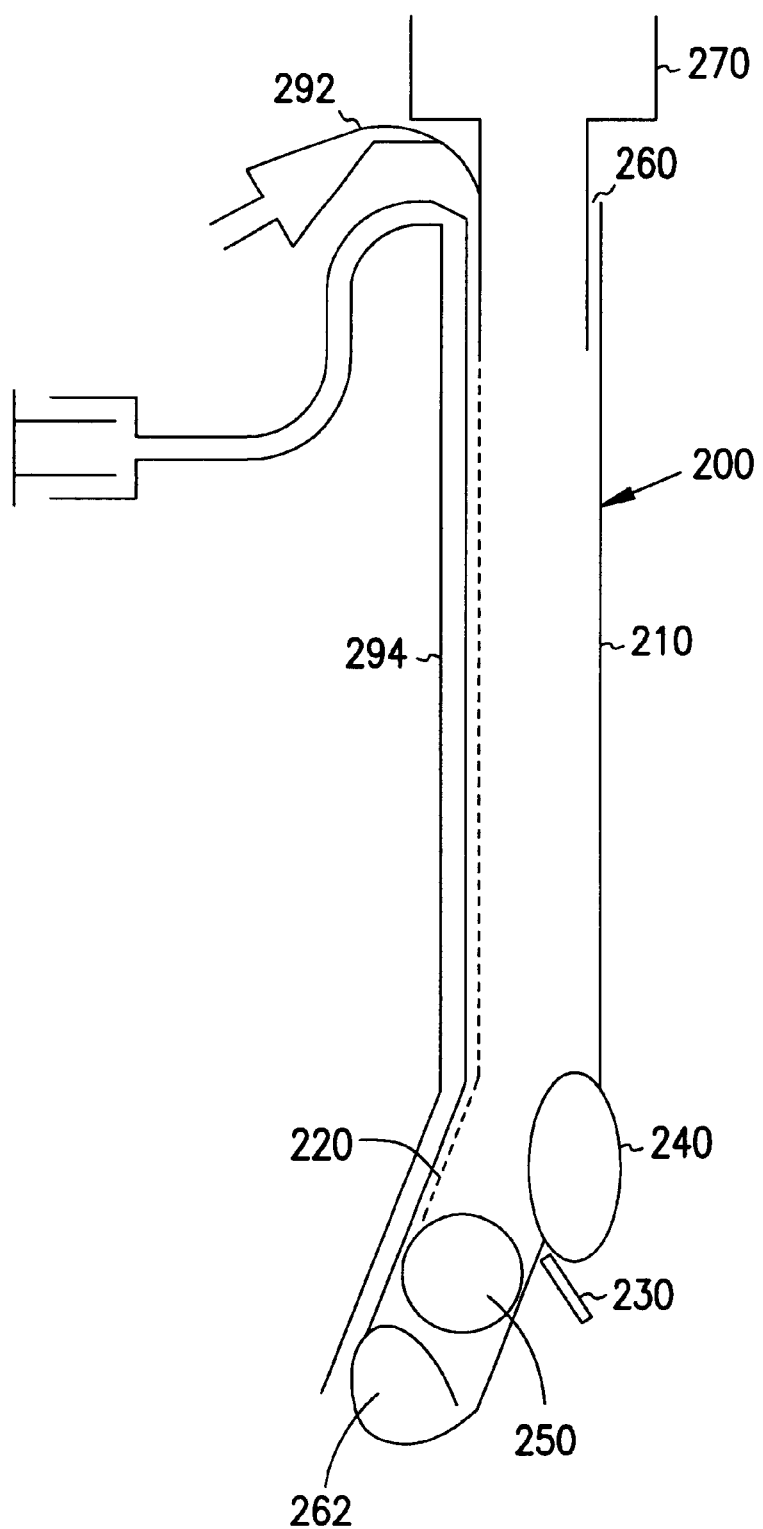
FIG. 1B is a schematic diagram of one preferred embodiment of the endotracheal tube invention for a right endotracheal tube.

FIG. 1B is a schematic diagram of one preferred embodiment of the endotracheal tube 200. The main difference between FIGS. 1A and 1B is that the endotracheal tube 200 shown in FIG. 1B is for a right endotracheal tube. In other words, the endotracheal tube 200 shown in FIG. 1B is for insertion into the right primary bronchus 110 so that the right lung 120 may be occluded or collapsed during a surgical procedure. The endotracheal tube includes a tracheal portion 210 and a bronchial portion 220. The bronchial portion 220 makes an angle with respect to the tracheal portion 210. It should be noted that the angle between the bronchial portion 220 and the tracheal portion 210 of the endotracheal tube 200 may be different than the angle between those two portions shown in FIG. 1A. Again, the angle is dependent upon the angle between the right primary bronchus 110 and the trachea within the particular patient. As is well known, the angle is age dependent, as well as dependent on whether the right bronchus 110 or the left bronchus 112 is being entered within the bronchial portion 220 of the endotracheal tube 200. The endotracheal tube 200 includes a carinal seating mechanism 230 and has an opening 240 near the carinal seating mechanism 230 which faces the opposite lung 122 and the opposite bronchus 112. Between the opening 240 and the distal end 262 of the endotracheal tube 200 is a intraluminal cuff or balloon 250 which can be inflated via the channel or small lumen 290 which has an inflation and deflation port 292 for a syringe which is positioned near the proximal end 260 of the endotracheal tube 200. The other end of the channel 290 is attached or in fluid communication with the balloon or intraluminal cuff 250. Another lumen or small channel 294 is provided which may function as a vent for the occluded lung or also function as a route to provide jet ventilation of one lung or oxygen insufflation. The lumen 294 has a luerlock which can be kept closed or open and may also incorporate a pop-off valve to release 30 to 60 cm water pressure. In essence, the endotracheal tube shown in FIG. 1B is substantially the same as the endotracheal tube shown in FIG. 1A with the exception that the endotracheal tube 200 shown in FIG. 1B is adapted for entering the right bronchus 110 of the patient.

Figure 2A:
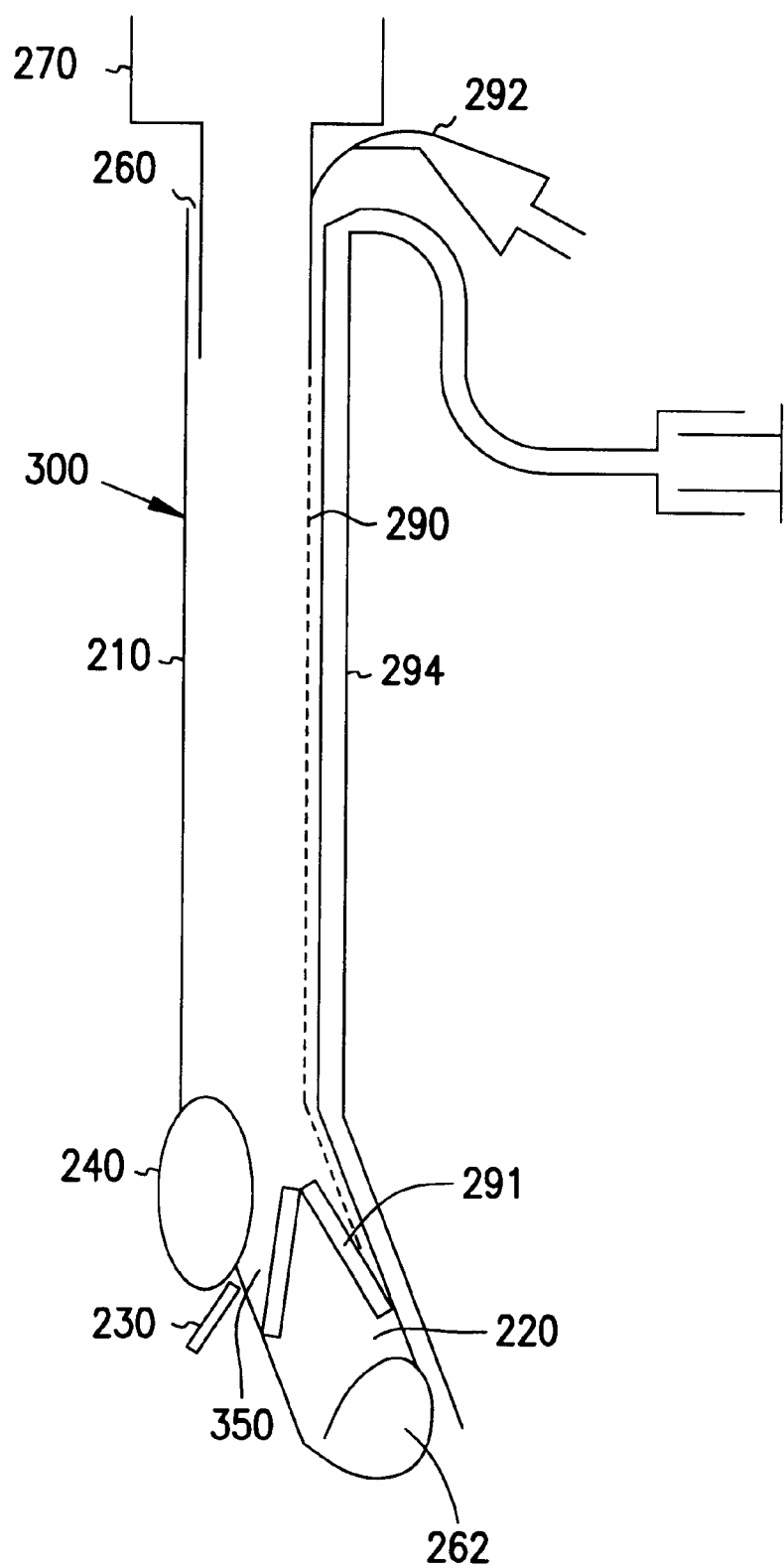
FIG. 2A is a schematic diagram of another preferred embodiment of the endotracheal tube invention for a left endotracheal tube.

FIG. 2A is a schematic diagram of another embodiment of the endotracheal tube 300 for insertion into the left bronchus 112. The endotracheal tube 300 is essentially the same as the endotracheal tube 200 shown in FIG. 1A. The main difference between the endotracheal tube 300 and the endotracheal tube 200 is that the balloon or intraluminal cuff 250 has been replaced with a foam-like or valve-like valve.

This is another method to block the bronchial portion of the tube. Instead of having an ordinary cuff like balloon, air inflation allows the activation of a valve which allows air from the lung to flow into the bronchus and then to the trachea but prevents air or fluid entry into the lung during position pressure or spontaneous breathing from the trachea to the bronchus. Deflation of this valve, like the cuff, will allow free communication of air or fluid between the bronchial extension and the tracheal lumen.

The foam cuff is another method to occlude the lumen of the bronchial extension. This tube uses a technology similar to the technology used in the intra luminal cuff. Activation of the foam cuff occludes with the injection of air by a syringe similar to that of the valve or air cuffs.

Figure 2B:
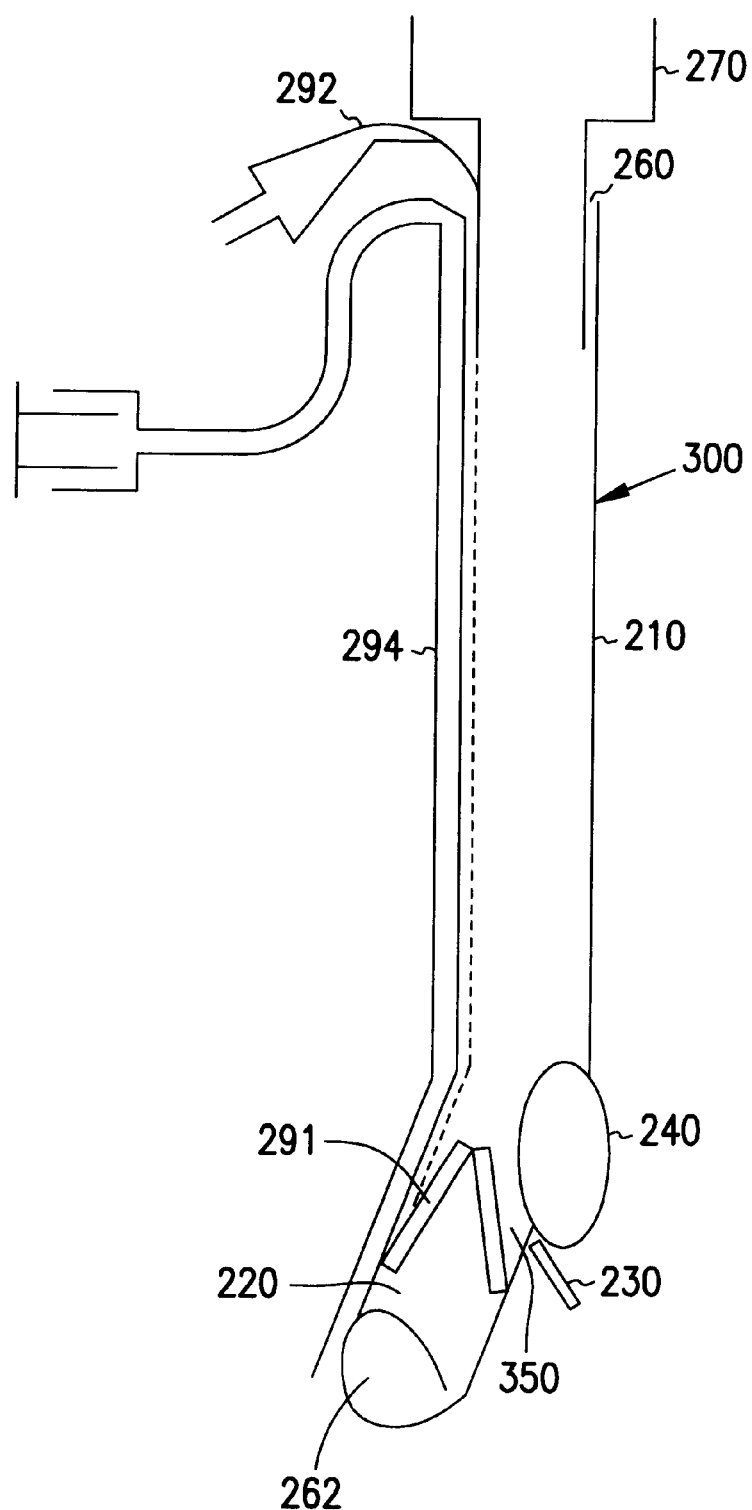
FIG. 2B is a schematic diagram of another preferred embodiment of the endotracheal tube invention for a right endotracheal tube.

FIG. 2B is a schematic diagram of another preferred embodiment of the endotracheal tube 300 which is for insertion into the left bronchus 112 of a patient. Again, the endotracheal tube 300 is essentially the same as the endotracheal tube 300 shown in FIG. 1B with the exception of the valve-like intraluminal cuff 350 which is positioned in the bronchial portion 220 of the endotracheal tube 200 between the opening 240 and the distal end 262 of the endotracheal tube 300. This is another method to block the bronchial portion of the tube. Instead of having an ordinary cuff-like balloon, air inflation allows the activation of a valve which allows air from the lung to flow into the bronchus and then to the trachea but prevents air or fluid entry into the lung during positive pressure or spontaneous breathing from the trachea to the bronchus. Deflation of this valve-like cuff will allow free communication of air or fluid between the bronchial extension and the tracheal lumen.

The foam cuff is another method to occlude the lumen of the bronchial extension. (Foam cuff technology for external cuffs has already been described; in this tube we are suggesting similar technology as an intraluminal cuff.) Activation of the foam cuff occurs with the injection of air by a syringe similar to that of the valve or air cuffs.

Figure 3A:
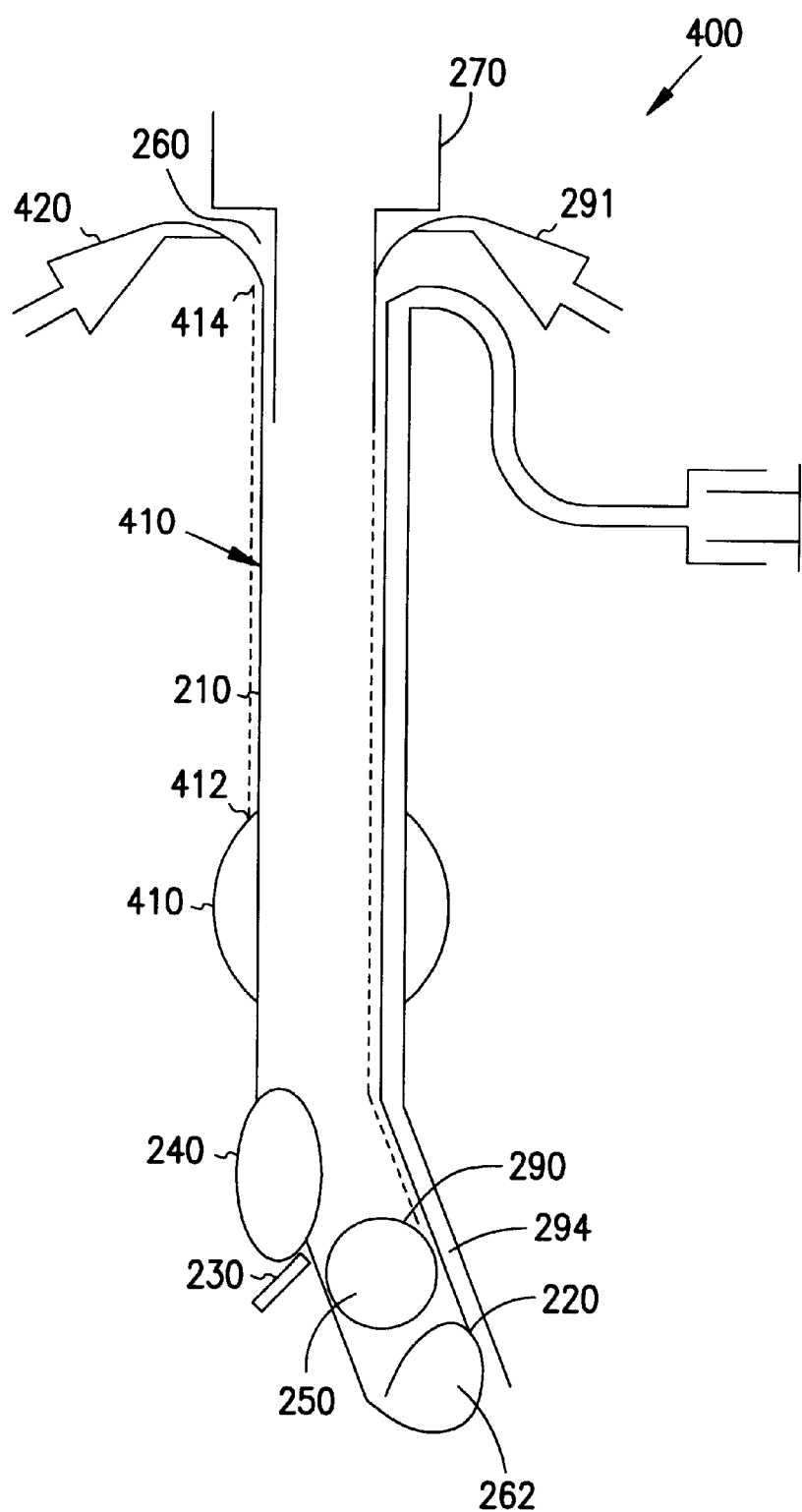
FIG. 3A is a schematic diagram of yet another preferred embodiment of the endotracheal tube invention for a left endotracheal tube.

FIG. 3A is a schematic diagram of yet another preferred embodiment of an endotracheal tube 400 which is for insertion into the left bronchus 112 of a patient. The endotracheal tube 400 shown in FIG. 3A is very similar to the endotracheal tube 200 shown in FIG. 1A. The elements of the endotracheal tube 400 are substantially the same as the elements of the endotracheal tube 200 shown in FIG. 1A. As a result, only the differences between the endotracheal tube 400 and the endotracheal tube 200 will be described with respect to FIGS. 3A and 3B. The main difference between the endotracheal tube 400 and the endotracheal tube 200 is that the endotracheal tube 400 includes a tracheal cuff 410. A channel or small lumen 412 is attached to the tracheal cuff at one end. At the other end of the small lumen 412 and 414 is an external cuff inflation and deflation port 420 which is adapted to receive a syringe which is used to inflate or deflate the tracheal cuff 410. The tracheal cuff 410 is used to seal off the trachea 100 of the patient to prevent gases from going up or down the trachea or around the tracheal tube 400. The tracheal cuff 410, when inflated, also stabilizes the endotracheal tube 400 within the trachea of the patient.

Figure 3B:
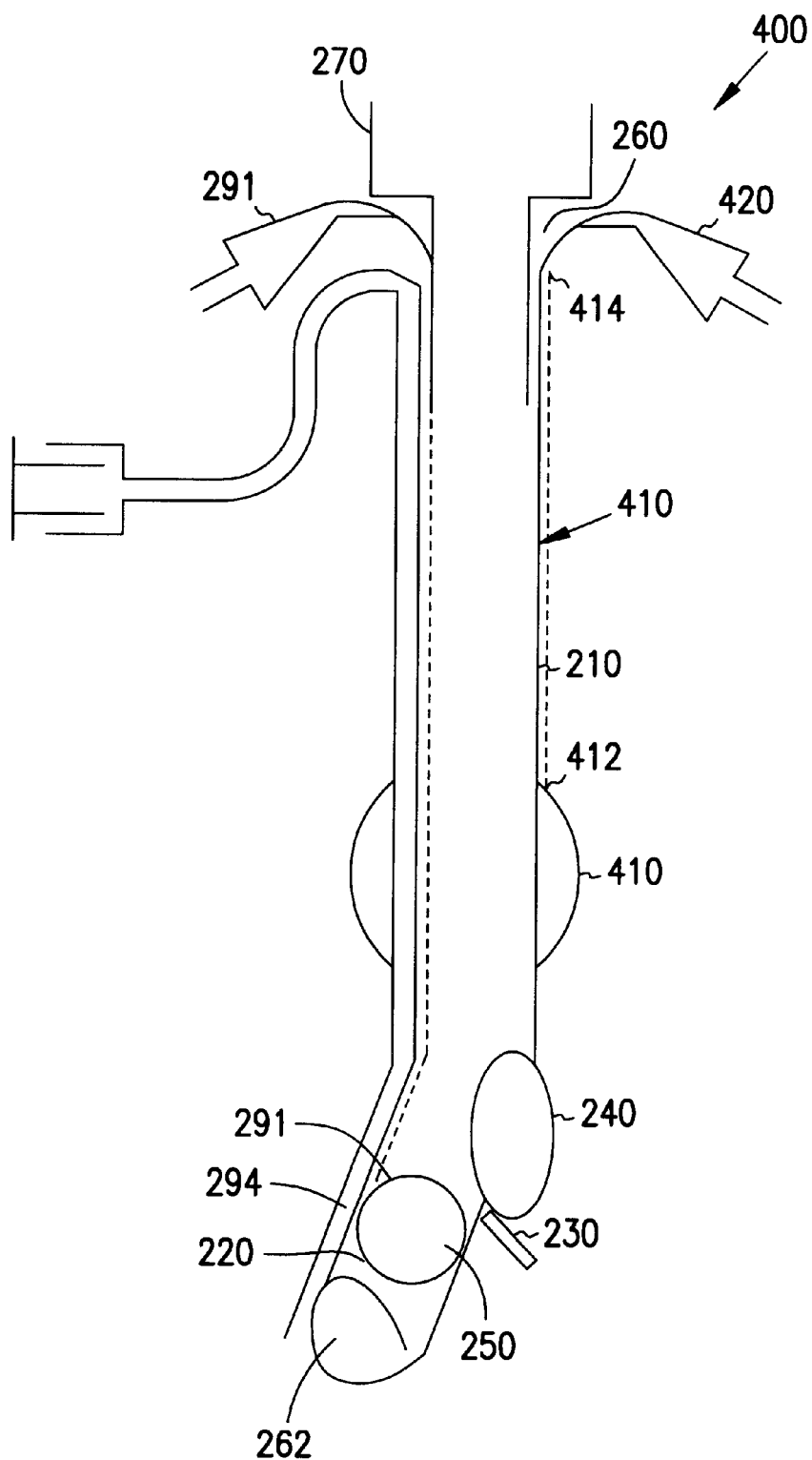
FIG. 3B is a schematic diagram of yet another preferred embodiment of the endotracheal tube invention for a right endotracheal tube.

FIG. 3B is a schematic diagram of the endotracheal tube 400 which is adapted for insertion into the right bronchus 110 of a patient. Again, the essential difference between the endotracheal tube 400 shown in FIG. 3B and the endotracheal tube 200 shown in FIG. 1B is that it includes the tracheal cuff 410, the channel or small lumen 412 having an end 414 near the proximal end of the endotracheal tube 400. At the end 414 of the lumen 412 is a port 420 adapted to receive a syringe used to inflate or deflate the external cuff 410. It should be noted that the lumen 410 is in fluid communication with the tracheal cuff 410.

Figure 4A:
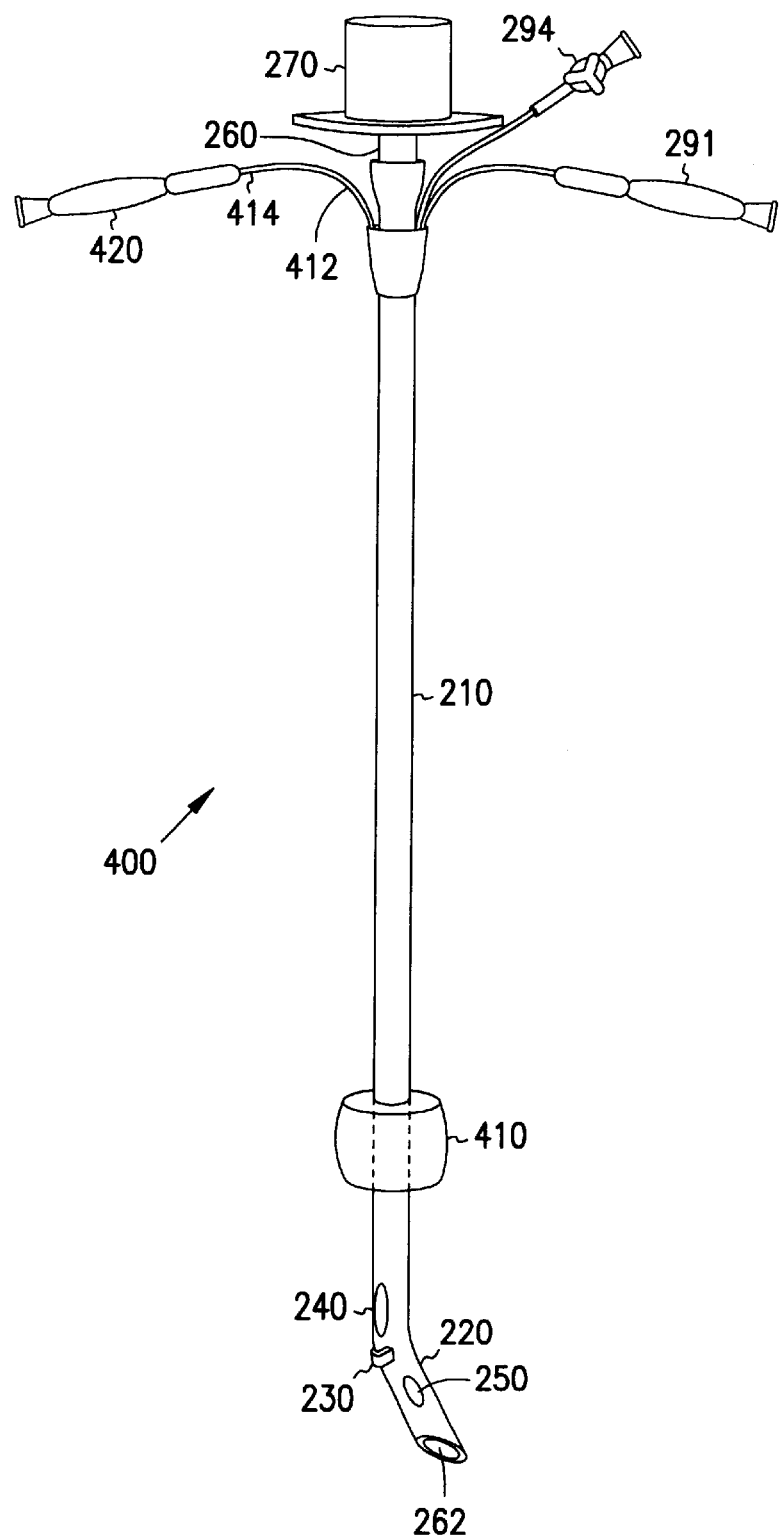
FIG. 4A is an isometric view of the preferred embodiment of the endotracheal tube invention for a left endotracheal tube depicted schematically in FIG. 3A with the internal balloon in a deflated state.

FIG. 4A is an isometric view of the preferred embodiment of the endotracheal tube 400 shown in FIG. 3A. In FIG. 4A, the internal balloon or intraluminal cuff 250 is shown in a deflated state. It should be noted that the balloon is attached to one side of the inner diameter of the bronchial portion 220 of the endotracheal tube 400. The end tracheal tube includes the port 420 which is injectable to inflate or deflate the tracheal external cuff 410. The tracheal tube 400 includes an injectable port to inflate or deflate the internal or intraluminal bronchial cuff 250. The intraluminal bronchial cuff 250 is also known as a balloon. The endotracheal tube 400 includes the carinal seating mechanism 230 made of a soft foam-like material and as can be seen, does not project too far out from the exterior surface of the endotracheal tube 400. The carinal seating mechanism 230 is located at the angulation between the tracheal portion 210 and the bronchial portion 220 of the endotracheal tube 400. Located above the angulation is the tracheal opening which faces the opposite bronchus of the bronchus into which the bronchial portion 220 will be placed.

Figure 4B:
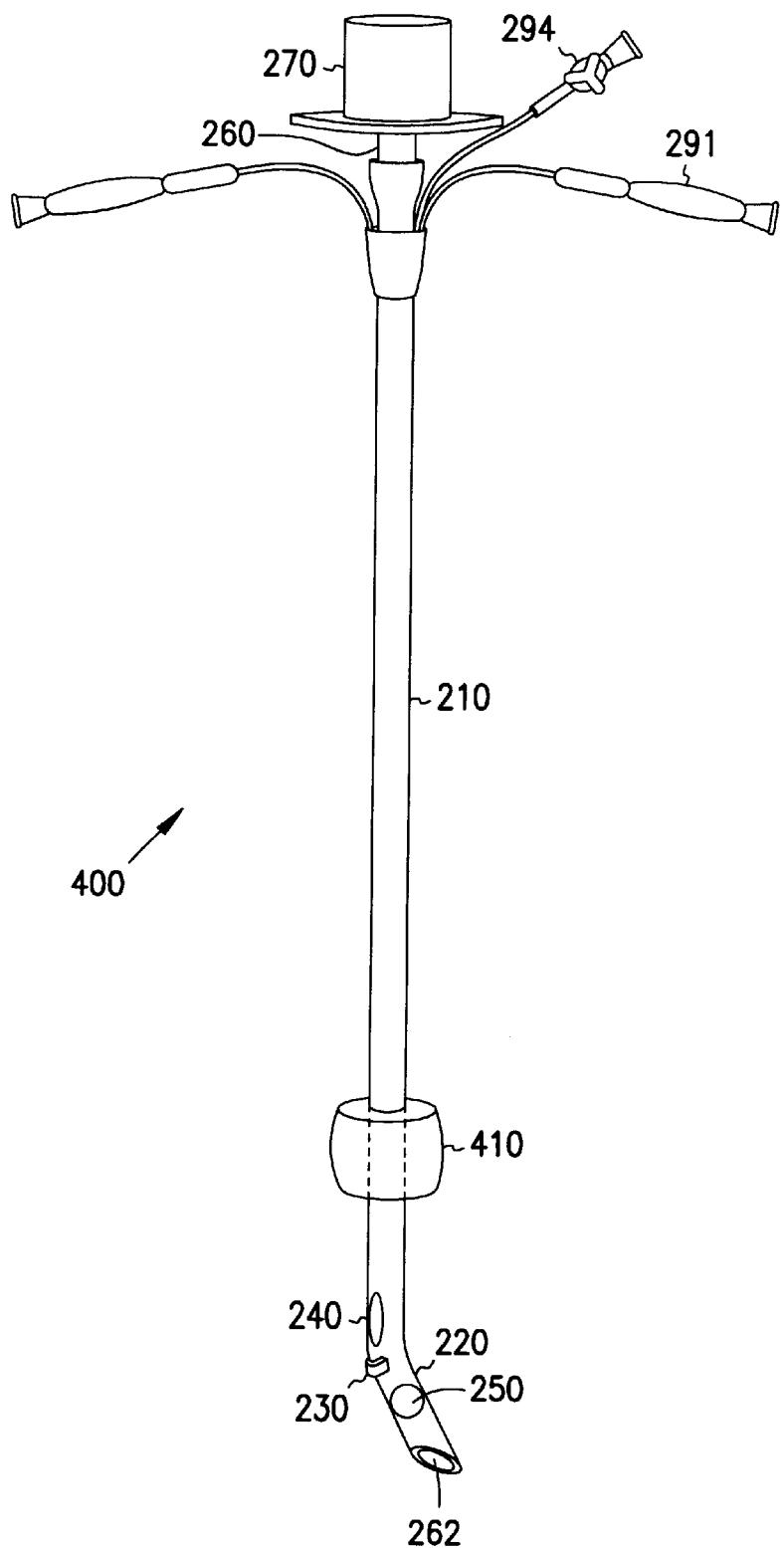
FIG. 4B is an isometric view of the preferred embodiment of the endotracheal tube invention for a left endotracheal tube depicted schematically in FIG. 3A with the internal balloon in an inflated state.

FIG. 4B is an isometric view of the preferred embodiment of the endotracheal tube 400 for a left bronchus which is depicted schematically in FIG. 3A. In FIG. 4B, the internal balloon or the internal bronchial cuff or intraluminal cuff 250 is inflated so that it blocks or occludes the bronchial portion 220 of the endotracheal tube 400. The only difference between FIGS. 4A and 4B is that the internal bronchial cuff or balloon 250 is in its inflated state and covers the entire inside diameter of the bronchial portion 220 of the endotracheal tube 400.

Figure 5A:
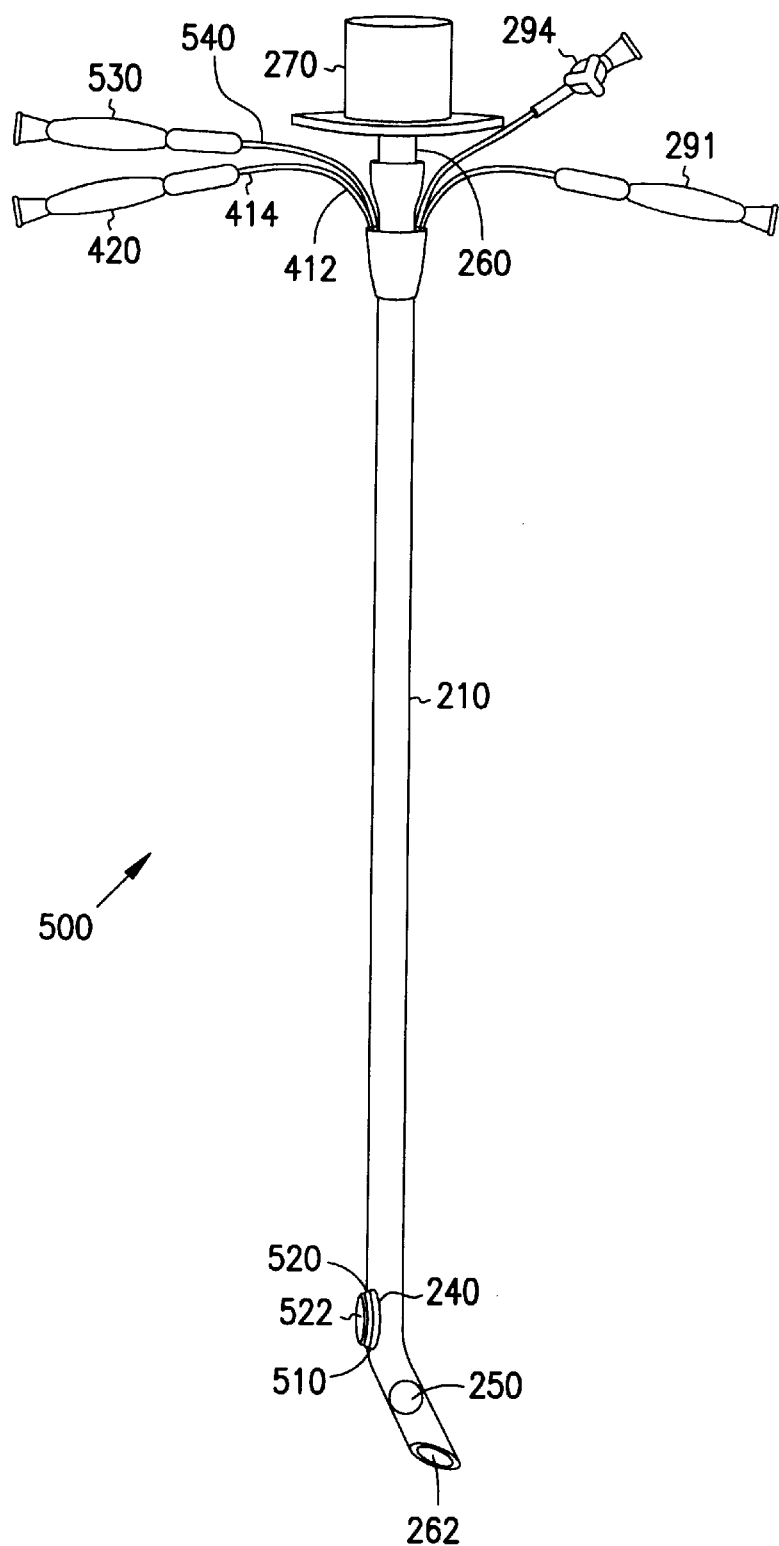
FIG. 5A is an isometric view of another preferred embodiment of the endotracheal tube invention for a left endotracheal tube with the internal balloon in an inflated state and with an inflatable bronchial extension in a deflated state.

FIG. 5A is an isometric view of another preferred embodiment of an endotracheal tube 500 which is adapted for insertion into the left bronchus 112. The endotracheal tube 500 is essentially the same as the endotracheal tube 200 shown in FIG. 1A. The main difference is that the endotracheal tube 500 includes an inflatable bronchial extension which has a first end 520 and a second end 522. The inflatable cuff is shown in a deflated state in FIG. 5A.

Figure 5B:
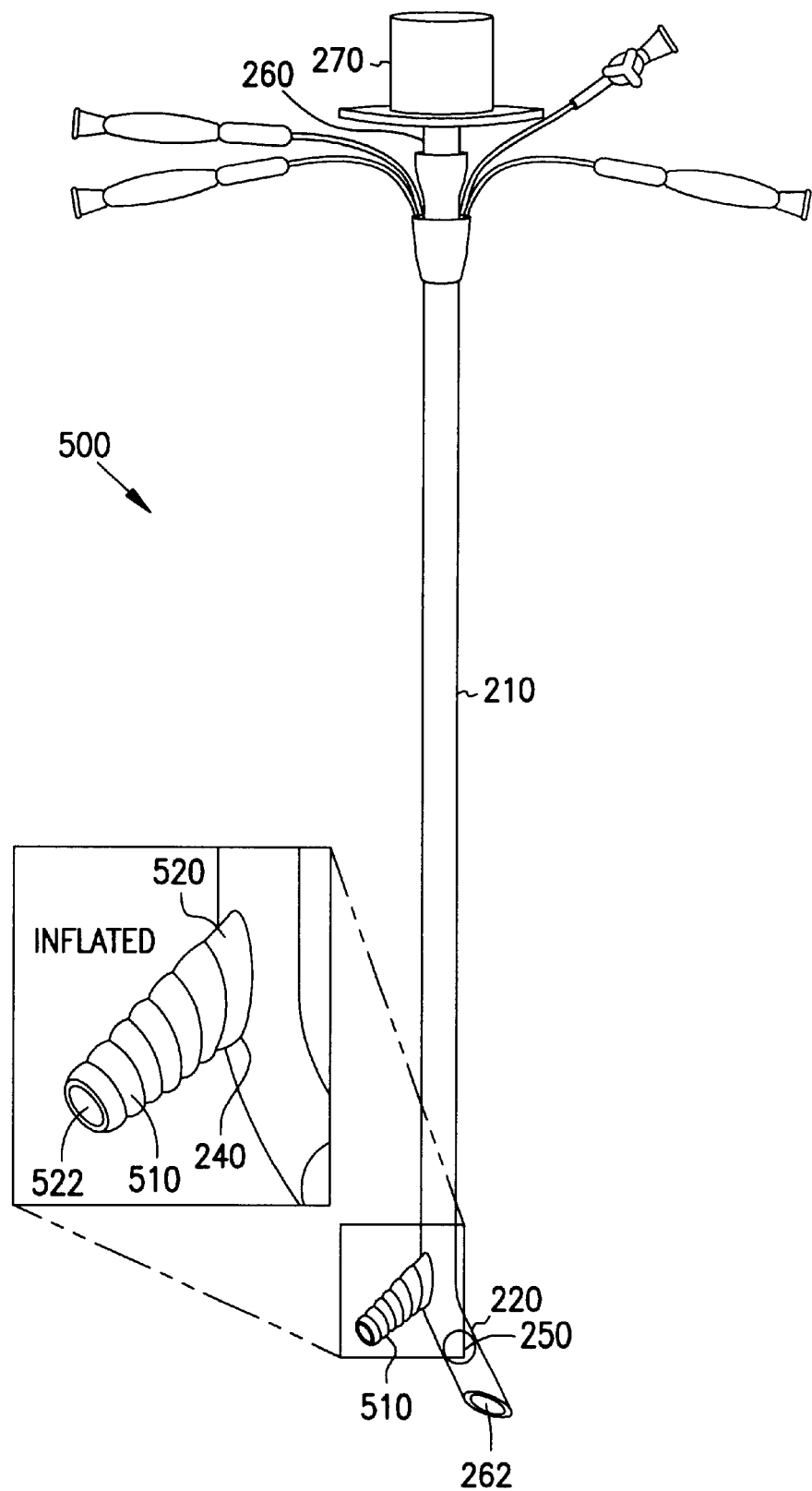
FIG. 5B is an isometric view of another preferred embodiment of the endotracheal tube invention for a left endotracheal tube with the internal balloon in an inflated state and with an inflatable bronchial extension in an inflated state.

FIG. 5B is the same isometric view of the endotracheal tube 500 with the inflatable bronchial extension 510 in an inflated state. Now referring both to FIGS. 5A and 5B, the endotracheal tube 500 will now be further discussed. The discussion will generally be limited to the differences between the endotracheal tube 500 and the endotracheal tube 200. The endotracheal tube 500 includes an inflatable bronchial extension 510. The inflatable bronchial extension 510 has an opening 520 and an opening 522. The opening 520 is about the periphery of the opening 240 which occurs near the carina or near the angulation between the bronchial portion 220 and the tracheal portion 210 of the endotracheal tube 500. Still another difference is that the carinal seating mechanism 230 is absent from the endotracheal tube 500. In essence, the inflatable bronchial extension 510 replaces the carinal seating mechanism 230.

The endotracheal tube 500 also includes an additional channel or lumen 540 which has an end attached to the inflatable bronchial extension 510 and which has another end to which a port for a syringe for inflation and deflation of the bronchial extension member is attached. The lumen 540, the port 530 and the bronchial extension 510 are in fluid communication with one another. As can be seen from FIG. 5B, the inflatable bronchial extension is shaped somewhat like an accordion. As the inflatable bronchial extension member inflates, the accordion unfolds and the inflatable bronchial extension member 510 enters the main bronchus opposite the bronchus in which the bronchial portion 220 of the endotracheal tube 500 is extended into. The endotracheal tube 500 includes an injectable port to inflate and deflate the internal bronchial cuff or balloon 250. The injectable port 291 is attached to one end of a small lumen or channel and the other end is attached to the internal bronchial cuff or balloon 250. The endotracheal tube 500 also includes the injectable port to deflate and inflate a tracheal cuff 410. It should be noted that this port can be removed in an embodiment where the tracheal cuff is not provided. It should be also noted that the inflatable bronchial extension 5 10 has a memory such that when deflated, it returns to the position near the opening 240 in the endotracheal tube 500. This provides for less trauma upon removal of the endotracheal tube 500 from a patient and for reinsertion if necessary.

Figure 6A:
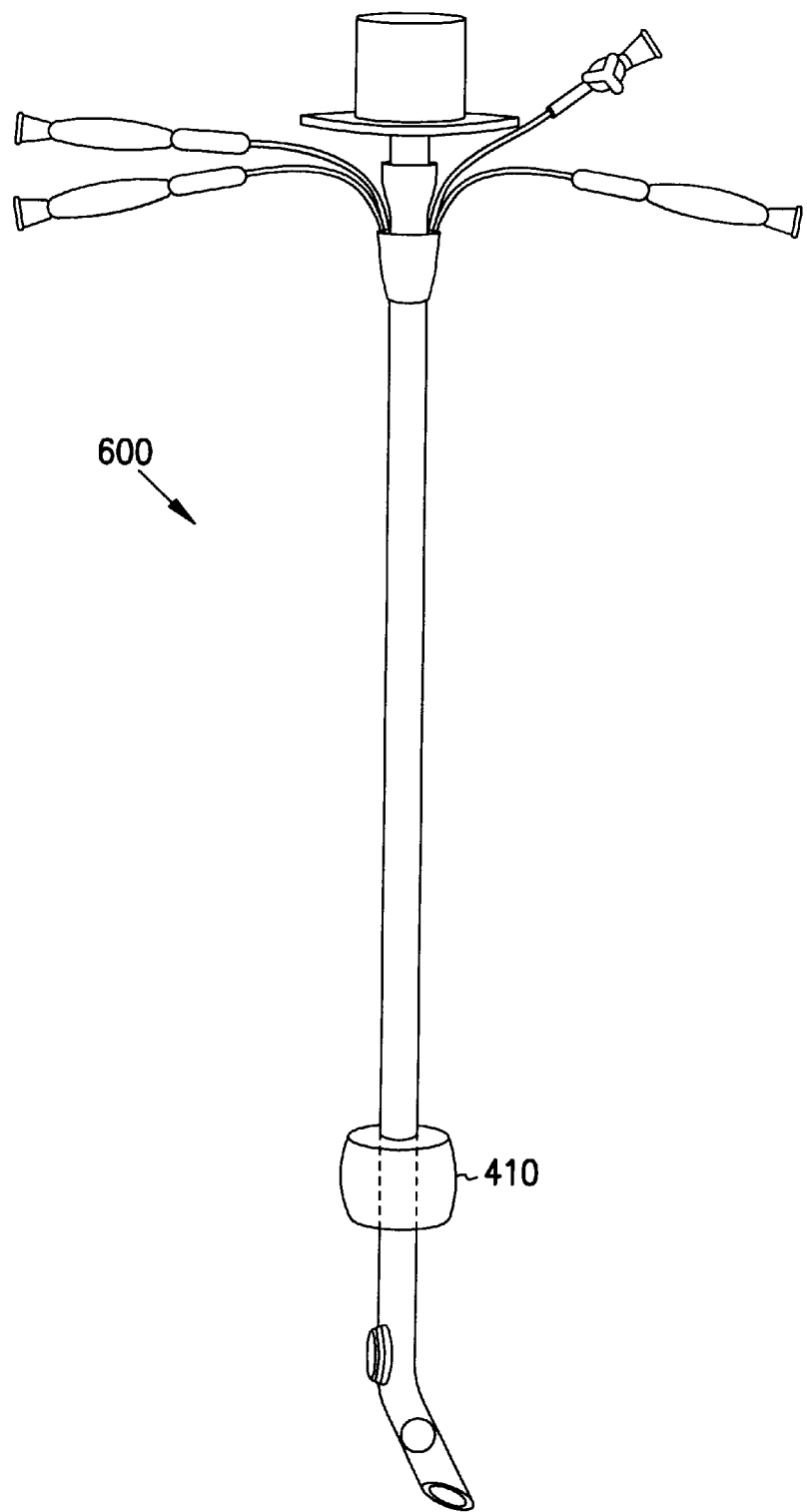
FIG. 6A is an isometric view of another preferred embodiment of the endotracheal tube invention for a left endotracheal tube depicted schematically in FIG. 5A with the internal balloon in an inflated state and with an inflatable bronchial extension in a deflated state.
Figure 6B:
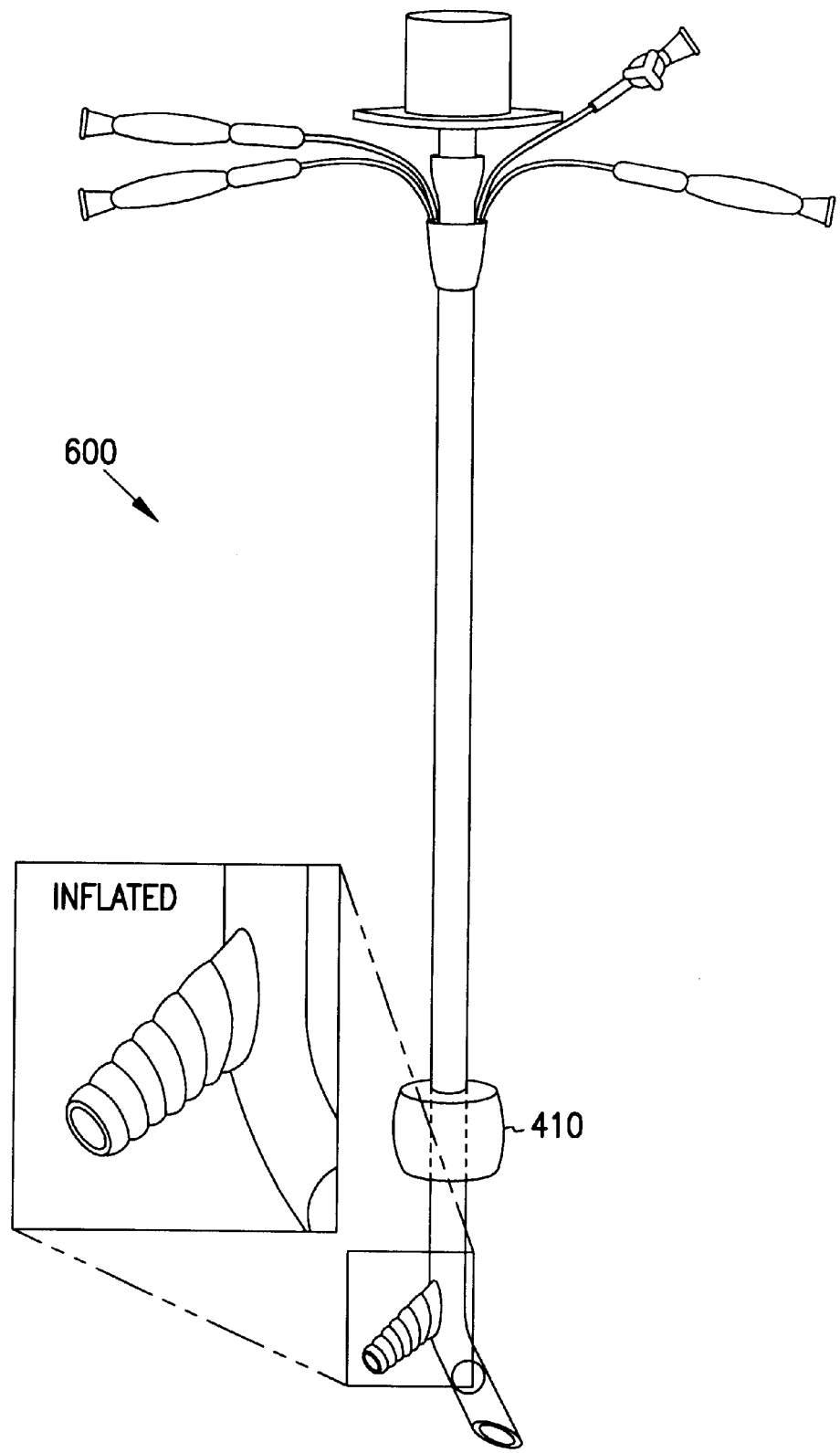
FIG. 6B is an isometric view of another preferred embodiment of the endotracheal tube invention for a left endotracheal tube depicted schematically in FIG. 5B with the internal balloon in an inflated state and with an inflatable bronchial extension in an inflated state.

FIGS. 6A and 6B show isometric views of another preferred embodiment of an endotracheal tube 600. The endotracheal tube in FIGS. 6A and 6B differs from the endotracheal tube 500 depicted in FIGS. 5A and 5B in that it includes an external tracheal cuff 410, the lumen between the cuff 410 and a port 420 used to inflate or deflate the external tracheal cuff 410.

Figure 7:
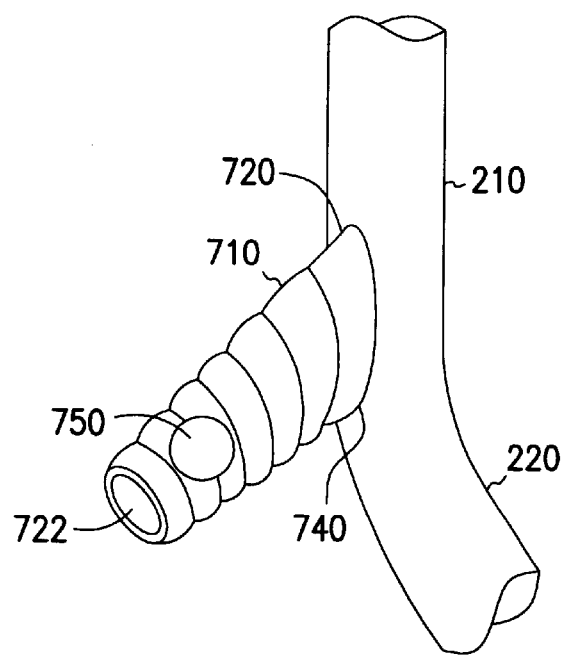
FIG. 7 is a schematic view of another preferred embodiment of the inflatable bronchial extension having an internal balloon associated therewith.

FIG. 7 is a schematic view of another embodiment of the inflatable bronchial extension 710. The inflatable bronchial extension 710 includes a first end 720 which is attached over and around the carinal opening 240 in the endotracheal portion 210 of the endotracheal tube. The bronchial extension 710 also includes another end 722 having an opening therein. An internal balloon or intraluminal cuff 750 is positioned along the length of the inflatable extension and within the inflatable extension. The balloon 750 is separately inflatable from the inflatable extension 710. As a result, there is an additional lumen or channel in fluid communication with the balloon 750 and having another end near the proximal end of the endotracheal tube which includes a port for inflating or deflating the balloon 750. By inflating the balloon 750, the inflatable bronchial extension is occluded and the lung associated with the bronchus and to which the bronchial extension extends can be collapsed for various surgical procedures.

Figure 8:
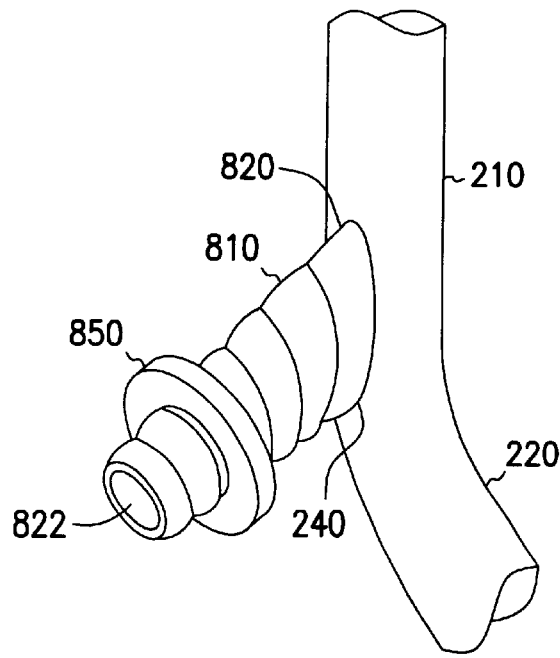
FIG. 8 is a schematic view of another preferred embodiment of the inflatable bronchial extension having an external cuff associated therewith.

FIG. 8 is a schematic view of another view of another preferred embodiment of an inflatable bronchial extension 810. The bronchial extension 810 includes a first end 820 which is positioned over the carinal opening 240 in the tracheal portion 210 of the endotracheal tube. The bronchial extension also includes an open end 822 which extends into the main bronchus of the patient. Positioned along the length and external to the bronchial extension is an external bronchial cuff 850 which is separately inflatable from the bronchial extension 810. Accordingly, the bronchial cuff 850 has a separate channel or lumen and a port near the proximal end of the endotracheal tube which is used to inflate or deflate the bronchial cuff 850 positioned on the inflatable bronchial extension 810. The bronchial cuff 850 stabilizes the bronchial extension within the main bronchus into which it extends.

Figure 9:
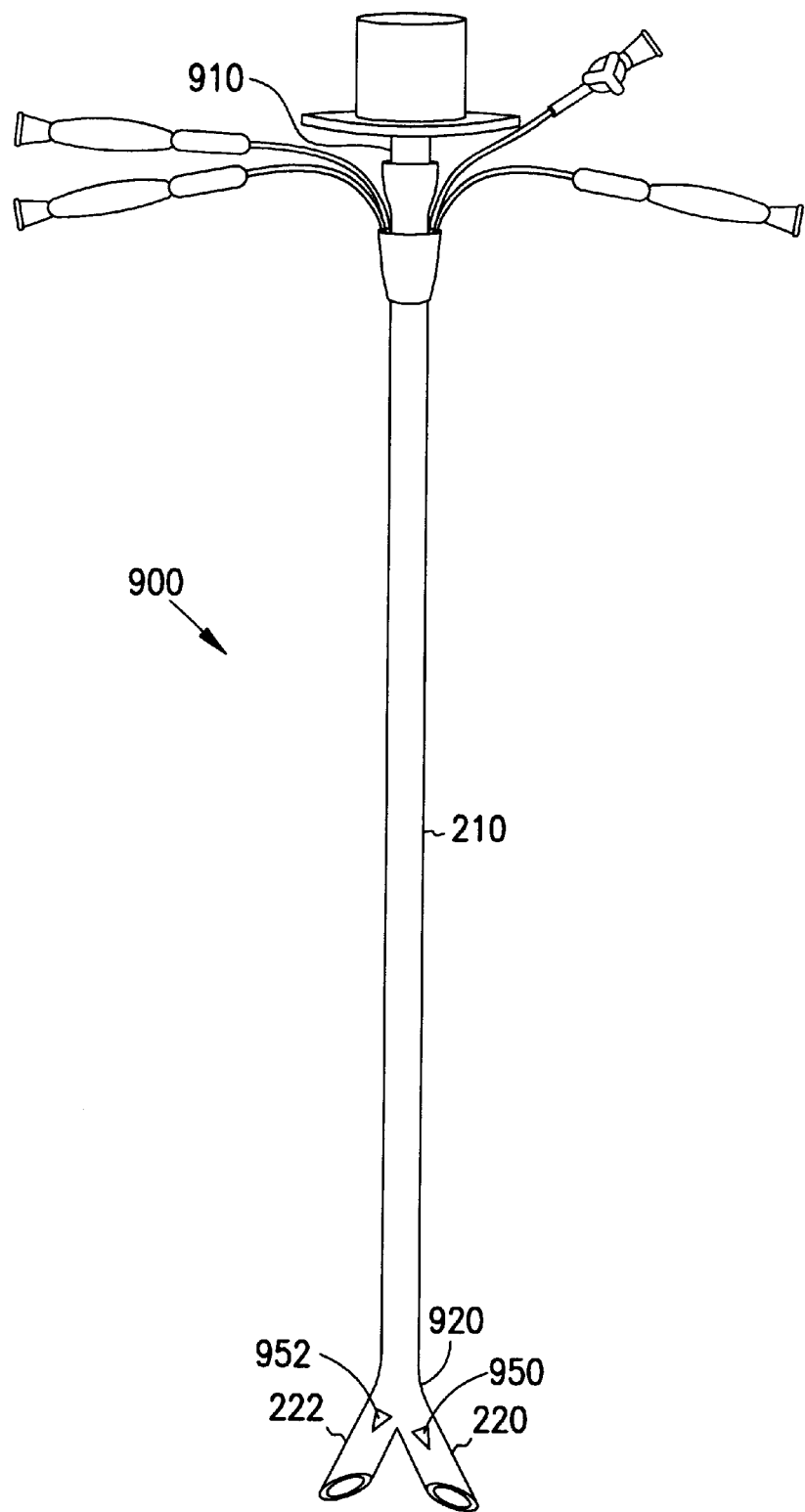
FIG. 9 is an isometric view of another preferred embodiment of an endotracheal tube invention with a bifid distal end.

FIG. 9 is an isometric view of another preferred embodiment of an endotracheal tube 900 having a bifid distal end. The endotracheal tube 900 includes a proximal end 910 and a bifid distal end 920. The endotracheal tube 900 includes a tracheal portion 210 and a pair of bronchial portions 220 and 222. In essence, the endotracheal tube 900 is a single lumen tube that breaks into a bitumen tube at its bifid distal end. Within each of the bronchial tubes 220 and 222 is an inflatable cuff or intraluminal cuff or balloon 950 and 952. Each of the balloons 950 and 952 is separately inflatable from the other balloon and therefore includes its own channel or small lumen and a port which is used to inflate or deflate the respective balloon 950, 952. It should be noted that the balloon 950, 952 can be replaced with a valve-like and/or a foam-like end which can be used to include either of the bronchial portions 220, 222, respectively.

Figure 10:
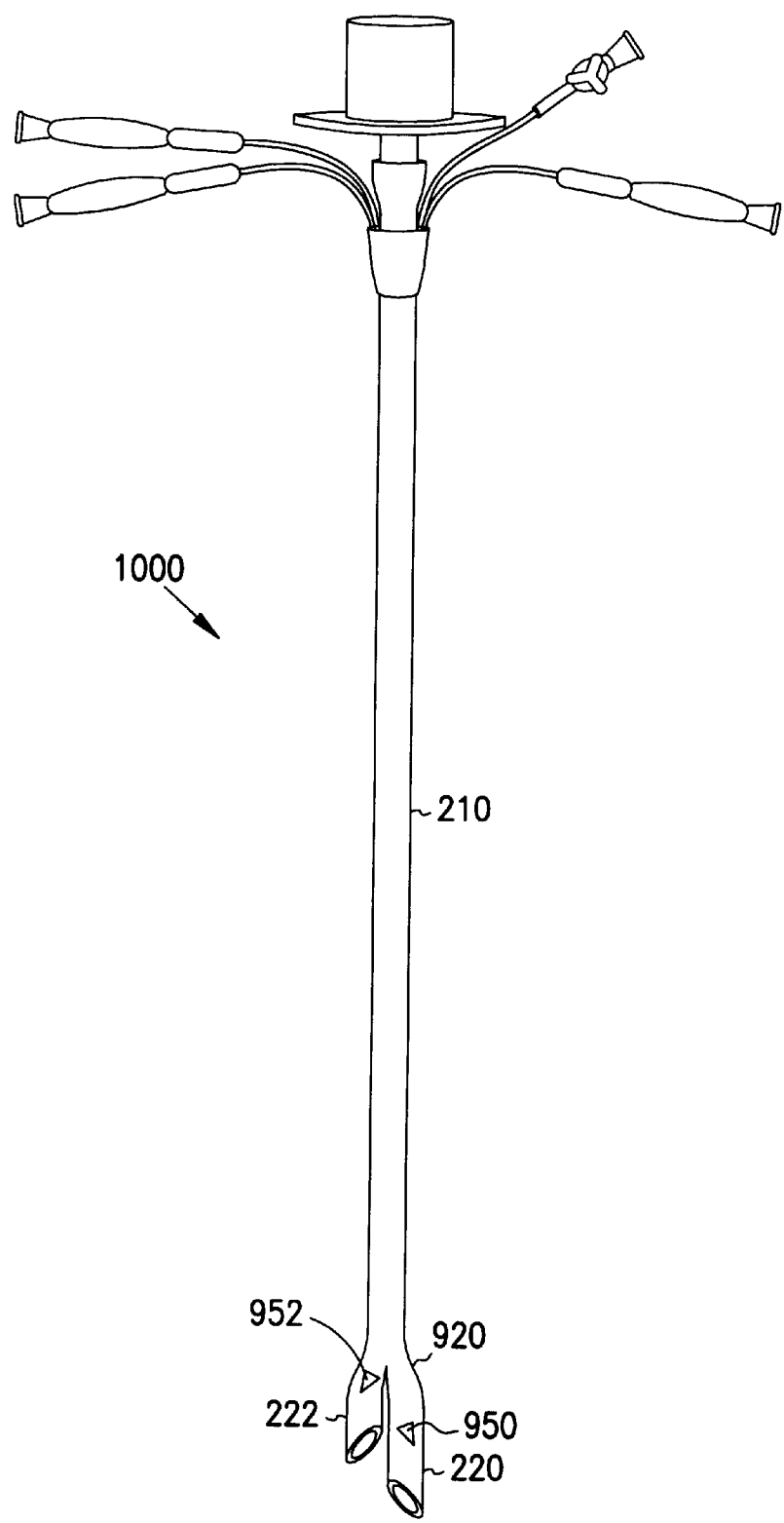
FIG. 10 is an isometric view of the preferred embodiment of an endotracheal tube invention with a bifid distal end of FIG. 8 with a stylus inserted therein.

FIG. 10 is an isometric view of the endotracheal tube 900 with the bifid end of FIG. 9 having a stylus 1000 inserted therein. The stylus 1000 extends through the tracheal portion 210 of the endotracheal tube 900 and into one of the bronchial portions, such as bronchial portion 220. The stylus 1000 is inserted into the endotracheal tube 900 while it is being inserted into the patient. The stylus allows straightening of the Y at the bifid end 920 of the endotracheal tube 900, which in turn allows for easier insertion down the larynx and trachea and into the bronchi. During insertion, the positioning of the bifid end is monitored and once it has reached a position closer to the bronchi with the proper orientation, the stylus 1000 is removed to allow for successful bronchial placement into both the left main stem bronchi and the right main stem bronchi.

Figure 11:
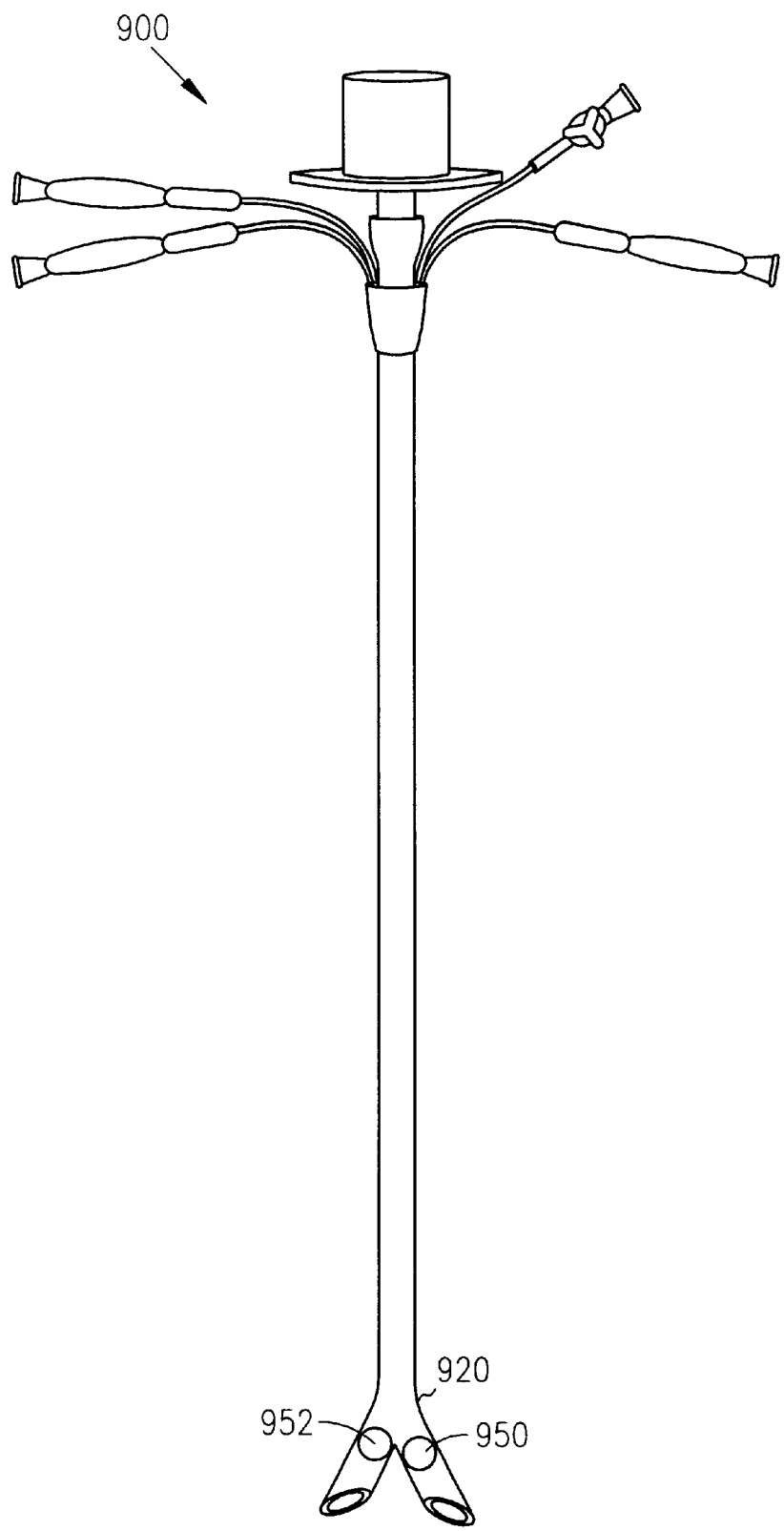
FIG. 11 is an isometric view of another preferred embodiment of an endotracheal tube invention with a bifid distal end of FIG. 8 with the stylus removed and both internal balloons inflated.

FIG. 11 shows the endotracheal tube 900 having the bifid distal end 920 with the stylus removed and both internal balloons 950 and 952 inflated. This is an orientation that might show up within a patient. However, it should be noted that one or the other of the balloons 950, 952 may be inflated at one time.

Each type of endotracheal tube described above would be available separately as a disposable sterilized endotracheal tube for one lung ventilation. Each package will also contain a suction catheter of matched diameter which will be long enough to extend from the oral end to 2 cm beyond the distal end of the endotracheal tube. The tube with the bifid end will also contain a stylet which will be preloaded so that the tube will be ready to use.

Conclusion

Advantageously, the preferred embodiments of the endotracheal tubes described can be inserted and quickly located in the correct position while minimizing trauma to the various portions of the patient. The time required to perform this procedure is also minimized which saves a surgeon time in the operating room and also minimizes the amount of time the patient is under anesthesia. The endotracheal tubes can be used to collapse one lung while ventilating the other lung. The endotracheal tubes also have a single lumen and can be used in all types of patients, especially pediatric patients where double lumen endotracheal tubes cannot provide the necessary air flow through two smaller lumens. There is also a need for catheters that can be sealed at their distal ends. The endotracheal tubes described allow ventilation of either one or both lungs in infants and small children. A left or right endotracheal tube may be used allowing occlusion of one lung. The non-ventilated lung will allow for better surgical access either to the lung itself or to structures surrounding the lung. In addition, the device should accommodate the larger trachea and bronchial airway of older children, young adults, as well as all adults. The design is simple and incorporates a single lumen tube capable of isolating each lung by an internal cuff or balloon. The single lumen allows for easier ventilation by being a larger lumen and favors ease of placement.

The endotracheal tube described also enhances procedures requiring anesthesia during thoracic surgery in infants and children: for example, surgery on the lung for tumors, abscesses, or other lung abnormalities; or around the lung, e.g., esophageal stricture or tumor. The device is particularly effective in preventing trans-bronchial spread of blood and infectious secretions during surgery, while providing improved surgical access to the affected lung. The endotracheal tube may also be useful in the pediatric intensive care unit, if one lung ventilation is desired.

The use of the described endotracheal tube provides one more (probably superior) option for physicians to incorporate one-lung ventilation during anesthesia and surgery or ICU management of pediatric and adult patients.

It is to be understood that the above description is intended to be illustrative and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. An endotracheal tube comprising:
    a proximal end;
    a distal end;
    a tracheal portion having an opening at the proximal end of the endotracheal tube;
    a bronchial portion attached at an angle to the tracheal portion, the bronchial portion having an opening at the distal end of the endotracheal tube, the bronchial portion and the tracheal portion of the endotracheal tube forming a single lumen; and
    a balloon positioned within the endotracheal tube, the balloon blocking flow of a gas through the bronchial portion of the endotracheal tube when inflated, the endotracheal tube having an opening positioned between the proximal end and the balloon.

2. The endotracheal tube of claim 1 wherein the opening in the endotracheal tube between the proximal end and the balloon is positioned to allow ventilation of a lung opposite the lung into which the bronchial portion is adapted to extend into.

3. The endotracheal tube of claim 1 further comprising a carinal seating mechanism.

4. The endotracheal tube of claim 3 wherein the carinal seating mechanism is comprised of foam rubber.

5. The endotracheal tube of claim 3 wherein the carinal seating mechanism extends beyond an outer periphery of the endotracheal tube at a distance such that it does not interfere with passing the endotracheal tube through a trachea of a patient, yet adapted to seat against a carina of a patient.

6. The endotracheal tube of claim 1 further comprising a carinal seating mechanism located near a junction between the tracheal portion and the bronchial portion of the endotracheal tube.

7. The endotracheal tube of claim 1 further comprising an external inflatable cuff positioned on the tracheal portion of the endotracheal tube.

8. The endotracheal tube of claim 1 further comprising one or more channels having a distal end and a proximal end, the distal end attached to an inflatable portion of the endotracheal tube and the proximal end of the one or more channels positioned near the proximal end of the endotracheal tube.

9. The endotracheal tube of claim 1 further comprising:
    a first external inflatable cuff positioned on the tracheal portion of the endotracheal tube; and
    a second external inflatable cuff positioned on the bronchial portion of the endotracheal tube.

10. The endotracheal tube of claim 1 wherein the angle between the bronchial portion and the tracheal portion of the endotracheal tube varies based on the age of the patient.

11. The endotracheal tube of claim 1 further comprising an inflatable bronchial extension tube having a first end and second end, one of the first end and the second end corresponding to the opening in the endotracheal tube positioned between the proximal end and the balloon and the other of the first end and the second end adapted to extend into a bronchus of a patient when inflated.

12. The endotracheal tube of claim 11 further comprising a cuff positioned around the other of the first end and the second end adapted to extend into a bronchus of a patient when inflated, the cuff separately inflatable from the inflatable bronchial extension tube.

13. The endotracheal tube of claim 11 further comprising a balloon positioned within the other of the first end and the second end adapted to extend into a bronchus of a patient when inflated, the balloon separately inflatable from the inflatable bronchial extension tube.

14. The endotracheal tube of claim 11 wherein the inflatable bronchial extension tube includes a bellows.

15. The endotracheal tube of claim 11 wherein the inflatable bronchial extension tube is adapted to extend at a selected angle from the tracheal portion of the endotracheal tube.

16. An endotracheal tube comprising:
    a proximal end;
    a tracheal portion having an opening at the proximal end of the endotracheal tube;
    a first bronchial portion having an attached end, the attached end attached at an angle to the tracheal portion, the first bronchial portion having a first open distal end;
    a second bronchial portion having an attached end, the attached end attached at an angle to the tracheal portion, the second bronchial portion having a second open distal end; and
    at least one balloon positioned within the endotracheal tube, the balloon blocking flow of a gas through one of the first and second bronchial portions of the endotracheal tube when inflated.

17. The endotracheal tube of claim 16 further comprising an external inflatable cuff positioned on the tracheal portion of the endotracheal tube.

18. The endotracheal tube of claim 16 further comprising:
a first external inflatable cuff positioned on the tracheal portion of the endotracheal tube; and
a second external inflatable cuff positioned on one of the first or second bronchial portions of the endotracheal tube.

19. The endotracheal tube of claim 16 further comprising:
a first external inflatable cuff positioned on the tracheal portion of the endotracheal tube;
a second external inflatable cuff positioned on the first bronchial portion of the endotracheal tube; and
a third external inflatable cuff positioned on the second bronchial portion of the endotracheal tube.

20. The endotracheal tube of claim 16 wherein the angle between the first bronchial portion and the tracheal portion of the endotracheal tube varies based on the age of the patient.

21. The endotracheal tube of claim 16 wherein the angle between the first bronchial portion and the tracheal portion of the endotracheal tube varies based on the age of the patient and wherein the angle between the second bronchial portion and the tracheal portion of the endotracheal tube varies based on the age of the patient.

22. The endotracheal tube of claim 16 wherein the at least one balloon positioned within the endotracheal tube is positioned within one of the first or the second bronchial portions of the endotracheal tube.

23. The endotracheal tube of claim 22 further comprising at least a second balloon positioned within the other of the first or the second bronchial portions of the endotracheal tube.

24. The endotracheal tube of claim 23 wherein the at least one balloon and the at least second balloon are independently inflatable.

25. The endotracheal tube of claim 22 further comprising at least one external cuff positioned on the tracheal portion of the endotracheal tube.

26. The endotracheal tube of claim 16 further comprising a stylus, the endotracheal tube adapted to receive the stylus through the tracheal portion and at least one of the first or second bronchial portions.

27. A method for inserting an endotracheal tube having a tracheal portion, and a bronchial portion, the tracheal portion and the bronchial portion formed as a single lumen, the bronchial portion attached at an angle to the tracheal portion, and a carinal seating mechanism comprising inserting the endotracheal tube into a trachea until the carinal seating mechanism is positioned near a site of the carina of a patient.

28. The method of claim 27 further comprising the step of guiding the endotracheal tube to a position where the carinal seating mechanism is positioned near the site of the carina of a patient using a fiberoptic device.

29. The method of claim 27 further comprising the step of verifying that the carinal seating mechanism of the endotracheal tube is positioned near the site of the carina of a patient using a fiberoptic device.

30. A method of inserting an endotracheal tube having a tracheal portion, a first bronchial portion attached at an angle to the tracheal portion, and a second bronchial portion attached at an angle to the tracheal portion, comprising:
inserting a stylus into the endotracheal tube, the stylus passing through the tracheal portion and into one of the first or the second bronchial portions of the endotracheal tube;
inserting the endotracheal tube through the trachea and inserting one of the first or second bronchial portions into a desired bronchus of the patient; and
removing the stylus.

31. The method of claim 30 further comprising using a fiberoptic device to guide the endotracheal tube to a position where one of the first bronchial portion or the second bronchial portion is positioned in a selected bronchus of the patient.

32. The method of claim 30 further comprising using a fiberoptic device to verify that the endotracheal tube is positioned such that one of the first bronchial portion or the second bronchial portion is positioned in a selected bronchus of the patient.

33. The method of claim 30 further comprising using a fiberoptic device to verify that the endotracheal tube is positioned such that both the first bronchial portion and the second bronchial portion are positioned in a selected bronchi of the patient.

\* \* \* \* \*